United States Patent [19]

Allen et al.

[11] Patent Number: 4,940,658
[45] Date of Patent: Jul. 10, 1990

[54] ASSAY FOR SULFHYDRYL AMINO ACIDS AND METHODS FOR DETECTING AND DISTINGUISHING COBALAMIN AND FOLIC ACID DEFICENCY

[75] Inventors: Robert H. Allen, Englewood; Sally P. Stabler, Denver, both of Colo.; John Lindenbaum, New York, N.Y.

[73] Assignee: University Patents, Inc., Westport, Conn.

[21] Appl. No.: 933,553

[22] Filed: Nov. 20, 1986

[51] Int. Cl.$^5$ .................... C12Q 1/00; G01N 24/00; A61K 31/68; A61K 31/495
[52] U.S. Cl. ............................. 435/4; 435/18; 436/173; 436/174; 436/8; 436/86; 436/120; 436/825; 514/52; 514/258
[58] Field of Search ............... 435/7, 4, 18; 436/505, 436/173, 8, 15, 9, 43, 63, 86, 89, 119, 120, 173, 174, 175, 825; 514/52, 258

[56] References Cited

U.S. PATENT DOCUMENTS

| 3,577,511 | 5/1971 | Luhby | 424/9 |
|---|---|---|---|
| 4,188,189 | 2/1980 | Allen | 23/230.3 |
| 4,279,886 | 7/1981 | Allen | 424/1 |
| 4,332,785 | 6/1982 | Allen et al. | 424/1 |
| 4,351,822 | 9/1982 | Allen | 424/1 |
| 4,427,780 | 1/1984 | Allen | 436/505 |
| 4,447,547 | 5/1984 | Allen et al. | 436/543 |
| 4,451,571 | 5/1984 | Allen | 436/505 |
| 4,467,037 | 8/1984 | Mawhinney | 436/89 |

FOREIGN PATENT DOCUMENTS 2248508 of 1975 France .
1435877 5/1976 United Kingdom .
2168478 6/1987 United Kingdom .

OTHER PUBLICATIONS

Babior, B. M. and H. F. Bunn, Harrison's Principles of Internal Medicine, Tenth Ed., R. G. Petersdorf et al., eds. (McGraw-Hill Book Co., N.Y., 1983), pp. 1853-1860.
Beck, W. S., Hematology, 3rd ed., W. J. Williams et al., eds. (McGraw-Hill Book Co., N.Y., 1983), pp. 434-465).
Beck, W. S., Cecil Textbook of Medicine, Vol. 1, 17th ed., J. B. Wyngaarden et al., eds. (W. B. Saunders Co., Philadelphia, 1985), pp. 893-900).
Biermann, C. J. et al., J. Chrom., (1986) 357:330-334.
Corbeel, L. et al., Eur. J. Pediatr., (1985) 143:284-290.
Davis, J. R., Am. J. Dis. Child, (1981) 135:566-567.
de John, A. P. J. M. et al., Biomedical Mass Spectrometry, (1980) 7(8):359-364.
Frader et al., New Eng. J. Med., (1978) 299(23):1319.
Goulian, M. et al., Am. J. Clin. Pathology, (1966) 46(3):390-391.
Graesbeck, R. et al., Acta Medica Scandinavica (1960) 167(4):289-296.
Higginbottom, M. C. et al., N. E. J. Med., (1978) 299(7):317-323.
Hoey, H. et al., J. Royal Soc. Med., (1982) 75:656-658.
Hoffbrand, A. V. et al., J. Clin. Path., (1966) 19:17-28.
Hollowell, J. G. et al., Lancet, (27 Dec. 69):1428-1429.
Knapp, D. R., Handbook of Analytical Derivatization Reactions, (John Wiley & Sons, N.Y. 1979).
Kolhouse, J. R. et al., N. E. J. Med., (1978) 199:785-792.
Labadarios, D. et al., J. Chrom., (1984) 310:223-231.
Lambert, H. P. et al., Q. J. Med., (1961) 30(117):71-90.
Lampkin, B. C. et al., Blodd, (1967) 30(4):495-502.
Lee, G. R., Textbook of Family Pactice, 3rd Ed., R. E. Rakel, ed., (W. B. Saunders Co., Philadelphia, 1984), pp. 1082-1091.

(List continued on next page.)

Primary Examiner—Esther M. Kepplinger
Assistant Examiner—Toni R. Scheiner
Attorney, Agent, or Firm—Yahwak & Associates

[57] ABSTRACT

Method for determining levels of sulfhydryl amino acids, particularly total homocysteine levels in samples of body tissue from warm-blooded animals, methods of detecting cobalamin and folic acid deficiency using an assay for total homocysteine levels, and methods for distinguishing cobalamin from folic acid deficiency using an assay for total homocysteine levels in conjunction with an assay for methylmalonic acid.

34 Claims, 7 Drawing Sheets

OTHER PUBLICATIONS

Malloy, M. H. et al., *Anal. Biochem.* (1981) 113:407–415.
Marcell, P. D. et al., *Anal. Biochem.*, (1985) 150:58–66.
Martensson, J., *Metabolism,* (1982) 31(5):487–492.
Matthews, D. M., *Clin. Sci.,* (1962) 22:101–111.
Metz, J. et al., Brit. J. Haemat. (1968) 14:575–592.
Mudd, S. H. et al., *The Metabolic Basis of Inherited Disease,* 5th ed., J. B. Stanbury et al., eds. (McGraw-Hill Book Co., N.Y., 1983), pp. 522–559.
Mudd, S. H., *Heritable Disorders of Amino Acid Metabolism: Patterns of Clinical Expression and Genetic Variation,* W. L. Nyhan, ed. (John Wiley & Sons, N.Y., 1974), pp. 429–451.
Norman, E. J. et al., *Blood,* (1982) 59(6):1128–1131.
Parry, T. E., *Brit. J. Haemat.,* (1969) 16:221–229.
Refsum, H. et al., *Clin. Chem.,* (1985) 31(4):624–628.
Rothenberg, S. P. et al., *New Eng. J. Med.,* (1972) 286(25):1335–1339.
Schilling. R. F. et al., *Clin. Chem.* (1983) 29(3):582–583.
Shahrokhi, F. et al., *J. Chrom.* (1968) 36:31–41.
Shipman, R. T. et al., *Lancet* (1969) 1(3):693–694.
Sievens, C. J., *Ugesk. Iaeger,* 125:1744 (1963).
Steel, R. G. D. et al., *Principles and Procedures of Statistics,* (McGraw-Hill Book Co., Inc., N.Y., 1960).
Zinn, A. B. et al., *Pediatric Res.* (1982) 16:740–745.
Alston, New. Eng. J. Med., 319(26), 1734 (1988).
Beck, New Eng. J. Med., 318(26), 1752–1754 (1988).
Brattstrom et al., Metabolism, 34(11), 1073–1077 (1985).
Brattstrom et al., Metabolism, 37(2), 175–178 (1988).
Carmel, J. Lab. Clin. Med., 110(3), 369–370 (1987).
Chanarin et al., Lancet, 2(8193), 505–508 (6 Sep. 1980).
Fleiss et al., New Eng. J. Med., 299(23), 1319 (1978).
Hershaft, New Eng. J. Med., 299(23), 1319–1320 (1978).
Kang et al., Metabolism, 36(5), 458–462 (1987).
Lindenbaum et al., Blood, 68, Suppl. 69a (Am. Soc. Hematology, 28th Ann. Meeting) (1986).
Lindenbaum et al., New Eng. J. Med., 318, 1720–1728 (1988).
Lindenbaum, Blood, 69(4), 624–627 (1983).
Lindenbaum et al., New Eng. J. Med., 319(26), 1734–1735 (1988).
Norman, GC-MS News, 12(5), 120–129 (1984).
Norman et al., New Eng. J. Med., 319(26), 1733 (1988).
Norman, J. Lab. Clin. Med., 110(3), 369 (1987).
Spivak, The Principles and Practice of Medicine, 21st ed., Chapter 49, pp. 482–488 (Appleton-Century-Crofts, Norwalk, Conn., (1984).
Stabler et al., Blood, 66, Suppl. 87a (Am. Soc. Hem. Meeting) (1985).
Stabler et al., J. Clin. Invest., 77, 1606–1612 (1986).
Stabler et al., Anal. Biochem., 162(1), 185–196 (1987), Chem. Abst. 107, 3728g, p. 349.
Stabler et al., Clin. Res., 35,635A (1987).
Weaver et al., Lancet, CCLXVI(6823), 1212–1213 (1954).
Williams et al., Anal. Biochem., 153, 372–379 (1986).
Laseter, J. L. et al., CA75: 148342g, vol. 75, p. 54 (1971).
Freed, C. R. et al., CA86: 117081u, vol. 86, p. 208 (1977).
Mudd, S. H. et al., CA70: 113151p, vol. 70, p. 150 (1969).
Frenkel, Eugene P. et al., CA86: 27496d, vol. 86, p. 172 (1977).

ASSAY FOR SULFHYDRYL AMINO ACIDS AND METHODS FOR DETECTING AND DISTINGUISHING COBALAMIN AND FOLIC ACID DEFICENCY

The research leading to this invention was partially funded by grants from the U.S. government.

This invention pertains to methods for quantifying sulfhydryl amino acid concentrations in a sample, for example methods of quantifying total homocysteine concentrations in samples of body tissue from a warm-blooded animal, and methods for determining whether said warm-blooded animal has a cobalamin deficiency, a folic acid deficiency, neither, or both.

BACKGROUND OF THE INVENTION

The sulfhydryl amino acids are metabolized according to a complex set of pathways as shown in FIG. 1.

As can be seen, methylation of homocysteine to form methionine via methionine synthetase requires methylcobalamin (Me-Cbl), also known as methyl-$B_{12}$. The methyl group is donated by $N^5$-methyltetrahydrofolate ($N^5$-MTHF), which is converted to tetrahydrofolate (THF). Conversion of methylmalonyl-CoA to succinyl-CoA via methylmalonyl-CoA mutase requires adenosyl-cobalamin, also known as adenosyl-$B_{12}$ as a cofactor. Thus cobalamin and folic acid are vital cofactors in sulfhydryl metabolism and cobalamin, but not folic acid, is a vital cofactor in methylmalonyl-CoA metabolism.

Accurate and early diagnosis of cobalamin and folate deficiencies in warm-blooded animals is important because these deficiencies can lead to life-threatening hematologic abnormalities which are completely reversible by treatment with cobalamin or folate, respectively. Accurate and early diagnosis of cobalamin deficiency is especially important because it can also lead to incapacitating and life-threatening neuropsychiatric abnormalities; administration of exogenous cobalamin always stops the progression of these abnormalities, almost always leads to significant improvement in symptoms, and frequently leads to their complete correction. The distinction between cobalamin and folate deficiency is often difficult because both deficiencies lead to indistinguishable hematologic abnormalities; the distinction is important because use of the proper vitamin results in the greatest improvement in hematologic abnormalities and, more importantly, only cobalamin will correct the neuropsychiatric abnormalities which are only seen in cobalamin deficiencies. The use of folic acid to treat cobalamin deficiency is extremely dangerous, since some, or all, of the hematologic abnormalities may improve, but neuropsychiatric abnormalities will not improve and may progress, or even be precipitated.

Chapters in leading medical textbooks and articles in leading medical journals teach that cobalamin deficiency should be suspected in individuals with significant anemia (i.e. decreased hematocrit or hemoglobin) in whom the red blood cells are macrocytic (i.e., mean cell volume (MCV) generally > 100 fl), or in individuals who have neurologic abnormalities consisting of peripheral neuropathy and/or ataxia. Many such textbook chapters or journal articles further state that the anemia is typically severe, i.e. hemoglobin $\leq 8$ g %, hematocrit < 25%, and size of the red blood cells is greatly increased to levels > 110 fl. [See, e.g., Babior, B. M., and H. F. Bunn, in *Harrison's Principles of Internal Medicine* (R. G. Petersdorf, R. F. Adams, E. Braunwald, K. J. Isselbacher, J. B. Martin, and J. D. Wilson, eds.)(McGraw-Hill Book Co., New York, 1983), pp. 1853–1860; Lee, G. R., and H. J. Gardner, in *Textbook of Family Practice*, 3rd Ed. (R. E. Rakel, ed.)(W. B. Saunders & Co., Philadelphia, 1984), pp. 1082–1091.]

Several laboratory tests have been reported as giving abnormal results in patients with cobalamin deficiency or folate deficiency. Such tests include measurements of red blood cell folate [Hoffbrand, A. V., et al., J. Clin. Path. 19:17(1966)] and the "dU suppression test"[Metz, J., et al., Brit. J. Haem. 14:575 (1968)], but neither is widely utilized. It has been known for more than twenty years that methylmalonic acid is excreted in increased amounts in the urine of most patients with cobalamin deficiency and that this abnormality is evidenced by only a few patients with folate deficiency. Because it is believed and taught that cobalamin deficiency should be suspected and can be diagnosed accurately based on the presence and degree of anemia, the presence and degree of macrocytosis, and by the presence and degree of depressed serum cobalamin levels, methylmalonic acid is rarely measured in patients suspected of being cobalamin-deficient. Indeed, it is taught in a leading textbook of medicine and in a leading textbook of hematology that in practice, assay of urinary methylmalonate is rarely necessary. [Beck, W. S., in *Hematology*, 3rd Ed. (W. J. Williams, E. Beutler, A. J. Erslev, and M. A. Lichtman, eds.) (McGraw-Hill Book Co., New York, 1983), pp. 434–465; Beck, W. S., in *Cecil Textbook of Medicine*, Vol. 1 (J. B. Wyngaarden and L. H. Smith, Jr., eds)(W. B. Saunders Co., Philadelphia, 1985), pp. 893–900.] While one recent journal article does advocate measurement of urinary methylmalonic acid [Norman, E. J., O. J. Martelo, and M. D. Denton, Blood 59(6):1128–1131 (1982)], analysis of the data in this paper reveals that 26 of the 27 cobalamin-deficient patients were anemic, that 23 of 27 patients had an elevated MCV, and that 12 of 12 patients whose serum cobalamin was measured with the standard improved serum cobalamin assay had values below 100 pg/ml. Thus these patients were all cobalamin-deficient according to standard diagnostic procedures and additional assays would normally have been judged to be unnecessary.

Assays for cobalamin and folate in serum or plasma are the most widely utilized and recommended tests for diagnosing and distinguishing cobalamin and folate deficiency. In the case of cobalamin deficiency, in which the normal range for serum cobalamin is about 200–900 pg/ml, several leading authors state that patients will not only have low serum cobalamin levels, but that these values will be below 100 pg/ml. [See, e.g., Babior, supra; Lee & Gardner, supra; Beck, in *Textbook of Medicine*, supra; and Beck, in *Hematology*, supra].

In 1978, it was discovered that cobalamin analogues are present in human plasma and that their presence could mask cobalamin deficiency because the radioisotope dilution assays for serum cobalamin then in use were not specific for true cobalamin. This problem could be corrected by using pure or purified intrinsic factor as the binding protein in the radioisotope dilution assay for cobalamin and this modification has almost totally replaced assays existing in 1978 that used a nonspecific cobalamin-binding protein. See, e.g., U.S. Pat. No. 4,188,189 (Allen), U.S. Pat. No. 4,351,822 (Allen), U.S. Pat. No. 4,451,571 (Allen), and Kolhouse, J. F., H. Kondo, N. C. Allen, E. Podell, and R. H. Allen, N.

Eng. J. Med. 299:785-792 (1978). These improved assays for serum cobalamin are now utilized in thousands of laboratories throughout the world and appear to give low values for all, or almost all, patients with cobalamin deficiency.

The improved assays have been severely criticized, however, because they frequently give low values in patients who lack any evidence of cobalamin deficiency. Because of this, experts in the field have taught that cobalamin deficiency should be considered, and serum cobalamin values should be obtained, only in patients who have hematologic or neurologic abnormalities that are typical of patients with cobalamin deficiency, as discussed above. Schilling and his coworkers, experts in the field of cobalamin deficiency and laboratory diagnosis, have stated:

"We conclude that the 'improved' vitamin $B_{12}$ assay kits will yield an increased proportion of clinically unexplained low results for serum $B_{12}$.

It seems prudent for scientific and economic reasons to measure serum vitamin $B_{12}$ only in patients who have hematological or neurological findings that suggest a reasonable probability of vitamin $B_{12}$ deficiency. Measuring serum $B_{12}$ as a screening test in the anemic or the geriatric population will result in a high proportion of low values that cannot be correlated with clinical disease."

Schilling, R. F., V. F. Fairbanks, R. Miller, K. Schmitt, and M. J. Smith, Clin. Chem. 29(3):582-583 (1983). Thus, the presently available widely used cobalamin assays may frequently provide low serum cobalamin levels in patients who are not truly cobalamin deficient. Such findings are confusing or misleading to the physician and may result in unneccessary and expensive further testing.

Thus, it is generally taught in the art that the clinical spectrum of cobalamin deficiency is relatively narrow and well-defined and that the possibility of cobalamin deficiency should only be considered in those who have concurrent hematological or neurological symptoms, i.e., usually those patients with moderately severe anemia accompanied by moderately severe macrocytosis, and in those patients with peripheral neuropathy and/or ataxia. Routine screening of the general population or those with only moderate anemia, or moderate macrocytosis, or other neuropsychiatric abnormalities, would lead to high numbers of false positives.

It has now been discovered that the clinical spectrum of cobalamin deficiency is much broader than previously recognized and that many cobalamin-deficient patients are not anemic, or only moderately anemic; that in many cases their red blood cells are not macrocytic, or only moderately macrocytic; that in many cases a variety of neurologic abnormalities other than peripheral neuropathy and ataxia are present; and that in many cases the serum cobalamin level is only slightly decreased and may actually be normal, even with the improved assays above using purified intrinsic factor. Accordingly, there is a need for an improved assay for cobalamin deficiency, preferably one in which cobalamin deficiency can be distinguished from folate deficiency.

SUMMARY OF THE INVENTION

Figure 1:
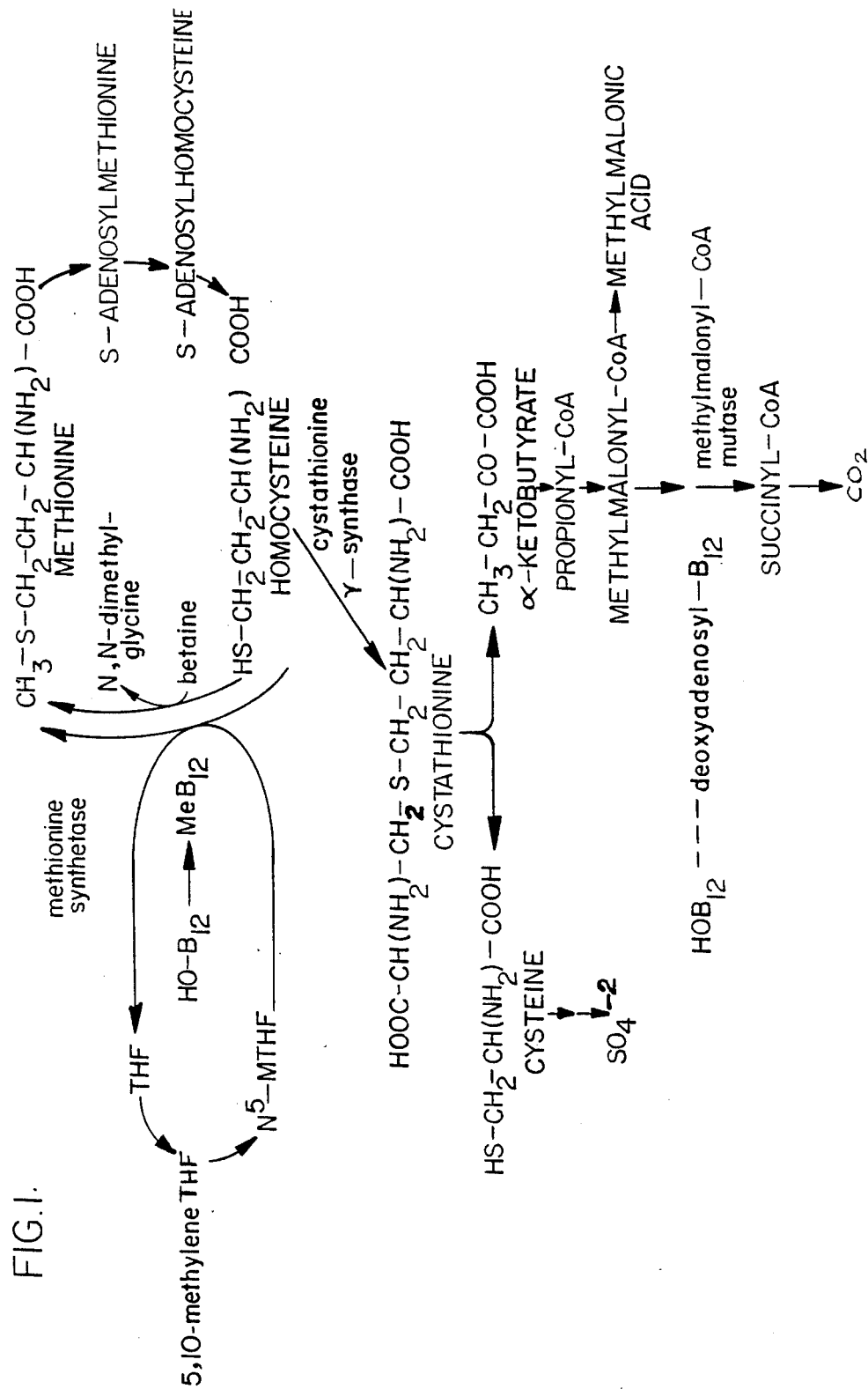
FIG. 1 is a representation of the pathways by which sulfhydryl amino acids are metabolized.

It has now been discovered that an elevated level of total homocysteine in tissues of warmblooded animals correlates both with cobalamin deficiency and with folic acid deficiency; an animal with elevated levels of total homocysteine is likely to have one or both deficiencies but the assay does not distinguish between the two.

In studies of sulfhydryl amino acid metabolism, normal human serum has been shown to contain small amounts of homocysteine-cysteine dimer and protein bound homocysteine. Homocystine has not been detected in normal serum but is present in small amounts in patients with renal insufficiency.

It was previously known that large amounts of homocystine are present in the serum and urine of children with inherited defects in cystathionine synthase who cannot convert homocysteine and serine to cystathionine. These patients also have increased amounts of methionine present in the serum [see, e.g, Mudd, S. H. and H. L. Levy, in *The Metabolic Basis of Inherited Disease*, 5th Ed. (J. B. Stanbury, J. B. Wyngaarden, D. S. Fredrickson, J. L. Goldstein, and M. S. Brown, eds.)(McGraw-Hill Book Co., New York, 1983), pp. 522-559. Large amounts of homocystine also present in the serum and urine of some children with inherited defects involving methionine synthetase, for instance certain children who cannot convert homocysteine and $N^5$-methyltetrahydrofolate to methionine and tetrahydrofolate, respectively. These patients have low levels of methionine in their serum. In these patients the inherited defects were due to (1) 5,10-methylenetetrahydrofolate reductase deficiency (inability to synthesize $N^5$-methyltetrahydrofolate, one of the substrates for methionine synthetase); (2) inability to synthesize methyl-cobalamin, a required cofactor for methionine synthetase; and (3) defects in methionine synthetase itself [see, e.g, Mudd, S. H., in *Heritable Disorders of Amino Acid Metabolism: Patterns of Clinical Expression and Genetic Variation*, (W. L. Nyhan, ed.)(John Wiley & Sons, New York, 1974), pp. 429-451]. On the other hand, homocystine has not previously been detected in the urine or serum of other children with inherited defects involving methionine synthetase activity due to an inherited defect in the ability to transport cobalamin to cells (e.g. transcobalamin II deficiency), or to an inherited defect in the intracellular transport of cobalamin where cobalamin is trapped within lysosomes. Large amounts of homocysteine or homocystine have been found in the serum and urine of a few children with life-threatening cobalamin deficiency [see, e.g., Shipman, R. T., R. R. W. Townley, and D. M. Danks, Lancet 1(2):693-694(1969); Frader, J., B. Reibman, and D. Turkewitz, N. Eng. J. Med. 299:1319(1978); Mudd, S. H., in *Heritable Disorders,* supra; Mudd, S. H., in *Metabolic Basis,* supra; Hollowell, J. G., Jr., W. K. Hall, M. E. Coryell, J. McPherson, Jr., D. A. Hahn, Lancet Dec. 27, 1969, p. 1428; Higgenbottom, M. C., L. Sweetman, and W. L. Nyhan, N. Eng. J. Med. 299(7):317-323 (1978); Davis, J. R., J. Goldenring, and B. H. Lubin, Am. J. Dis. Child. 135:566(1981); Hoey, H., J. C. Linnell, V. G. Oberholzer, and B. M. Laurance, J. Royal Soc. Med.75:656 (1982)]. In other infants with life-threatening cobalamin deficiency, amino acids in urine and/or serum were found to be normal and no homocystine was found [see, e.g., Graesbeck, R., R. Bordin, I. Kantero and B. Kuhlbaeck, Acta Medica Scandinavica 167(4):289 (1960); Lampkin, B. C. and A. M. Mauer, Blood 30(4):495 (1967); Lambert, H. P., T. A. J. Prankerd, and J. M. Smellie, Q. J. Med. 30(117):71(1961); Sievens, C. J., Ugesk. laeger 125:1744 (1963)] nor was it found in the urine of a child with life-threatening folate deficiency [Corbeel, L., G. Van den Berghe, J. Jaeken, J. van Tornout, N. R. Eeckles, Eur. J. Ped. 143: 284–290(1985)]. Homocystine has not previously been reported in the serum or urine of children with moderate or mild cobalamin or folate deficiencies nor has it previously been reported in the serum or urine of adults with life-threatening, moderate, or mild cobalamin or folate deficiencies.

It has also been discovered that the serum folate level is not reduced in many alcoholic patients with folate deficiency and that the measurement of total homocysteine provides an additional and more accurate indication of folate deficiency in many of these patients. It was previously known that homocysteine was elevated in the urine and/or serum of some children with inherited deficiency of folate metabolism [see, e.g. Mudd, S. H., in *Heritable Disorders,* supra; Mudd, S. H. in *Metabolic Basis,* supra], but it was not previously known that homocysteine was elevated in the urine or serum of children or adults with folate deficiency.

It has additionally been discovered that it is possible to determine whether an animal has cobalamin deficiency, folic acid deficiency, both, or neither, based on a combination assay comparing total tissue homocysteine and methylmalonic acid levels with normal levels. While both folic acid deficiency and cobalamin deficiency result in elevated total homocysteine levels, cobalamin deficiency will also elevate methylmalonic acid levels whereas folic acid deficiency will not. It was previously known that methylmalonic acid is elevated in the serum and/or urine of many children with inherited defects in cobalamin metabolism or cobalamin transport and in urine of children and adults with varying degrees of cobalamin deficiency [see, e.g., Beck, W. S., in *Hematology,* supra]. However, it has not previously been known or suggested to use an assay for methylmalonic acid in combination with an assay for homocysteine to diagnose and/or distinguish cobalamin and folate deficiencies. We have now discovered this combined assay is in fact extremely useful in diagnosing cobalamin deficiency in patients with varying degrees of anemia, macrocytosis, depression of the serum cobalamin level, and varying kinds of neuropsychiatric abnormalities.

It has been discovered that elevated levels of homocysteine in body tissue correlate with decreased levels of cobalamin and/or folic acid in said body tissue. Accordingly, assays for homocysteine can be used to determine the presence or absence of cobalamin and/or folic acid deficiency in warm-blooded animals. Suitable assays for this purpose include any assays capable of determining levels of homocysteine in body tissues, preferably body fluids, preferably urine or blood. Serum and plasma are particularly preferred.

There are several different known assays suitable for use in determining levels of homocysteine in urine or blood, however, none has ever before been used to detect cobalamin or folic acid deficiency. See, e.g, Saetre, R. and D. L. Rabenstein, Anal. Biochem. 90:684–692(1978), describing a method of measuring reduced and total cysteine in urine and total cysteine and homocysteine in the nonprotein fraction of plasma, in order to screen for certain congenital disorders of sulfur metabolism such as cystinuria, cystinosis, and homocystinuria and in the monitoring of their treatment. This method comprises subjecting a sample of body fluid to high performance liquid chromatography with an electrochemical detector set to respond to thiol groups, and comparing the results with a standard curve to determine the amount of target compound present in the original sample. In this procedure standards are run separately rather than simultaneously mixed with the target compound; it is thus not possible to insure that the recovery of the target and standard are equivalent. Another suitable procedure, described by Refsum, H., S. Helland, and P. M. Ueland, Clin. Chem. 31(4):624–628 (1985) comprises converting any homocysteine present in the sample to labelled S-adenosylhomocysteine by exposure to radioactively labelled S-adenosine and S-adenosylhomocysteine hydrolase, and quantifying said labelled S-adenosylhomocysteine by appropriate detection means. Suggested uses include monitoring homocysteine metabolism in the management of malignant disease and during treatment with the antifolate drug methotrexate, monitoring of the inherited disease homocystinuria, and monitoring serum homocysteine in plasma of post-menopausal women. The procedure has never been used to monitor homocysteine to detect or measure cobalamin or folic acid deficiency. Again, the procedure uses no internal standard, and thus it is not possible to insure that the recovery of the target and standard are equivalent.

DETAILED DESCRIPTION OF THE INVENTION

A much more sensitive and accurate procedure for measuring levels of homocysteine in serum or urine is the following novel assay for total sulfhydryl amino acids. Sulfhydryl amino acids are those containing the —SH moiety, e.g. homocysteine (Hcys) of the formula

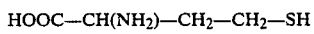
HOOC—CH(NH$_2$)—CH$_2$—CH$_2$—SH and cysteine (Cys) of the formula

HOOC—CH(NH$_2$)—CH$_2$—SH

Sulfhydryl compounds are characterized by a natural tendency to combine via disulfide bridges to form dimers, e.g. cystine of the formula

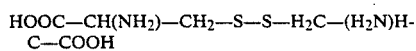
HOOC—CH(NH$_2$)—CH$_2$—S—S—H$_2$C—(H$_2$N)HC—COOH homocystine of the formula

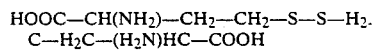
HOOC—CH(NH$_2$)—CH$_2$—CH$_2$—S—S—H$_2$C—H$_2$C—(H$_2$N)HC—COOH and homocysteine-cysteine of the formula

HOOC—CH(NH$_2$)—CH$_2$—CH$_2$—S—S—H$_2$C—(H$_2$N)HC—COOH

In the presence of proteins, both homocysteine and cysteine form complexes with free sulfhydryl groups on the protein molecule; in samples derived from tissues, such protein complexes may tie up most of the cysteine and homocysteine present. Assays for total sulfhydryl amino acids are complicated by the ease with which these amino acids form such complexes. Reduction is required for release and subsequent assay of protein bound sulfhydryl compounds but it appears likely that both amino acids might reform new disulfides to a significant extent after their initial reduction. The reformation of disulfide bonds could be quite variable and cannot be assessed or compensated for by the use of a nonsulfhydryl containing amino acid as an internal standard. Any assay for total sulfhydryl amino acids in a sample must take such dimers and complexes into account.

Accordingly, the present invention provides a preferred method of assaying the total cysteine and/or total homocysteine in a given sample using mass spectroscopy. The term "total cysteine" or "total homocysteine" refers to the total amount of cysteine or homocysteine, respectively, present in both free and complexed forms. For convenience, the following discussion will use homocysteine as an example, but the same procedure works for cysteine as well. The given sample containing endogenous homocysteine is combined with a sufficient amount of reducing agent to insure complete randomization of the endogenous homocysteine and the amount of total homocysteine is measured by appropriate means. Preferably, the given sample is first combined with an internal reference standard comprising a known amount of a compound which behaves analagously to the homocysteine but which is labelled with a stable isotope marker. A sufficient amount of reducing agent is added to insure complete randomization of the endogenous homocysteine and reference standard and the amounts of homocysteine and labelled reference standard present are measured with a mass spectrometer. Assuming that the endogenous homocysteine and reference standard occur at the same relative ratio throughout the procedure, this ratio can be calculated from the mass spectrometry readings and applied to the known amount of standard in the original sample to calculate the total amount of endogenous homocysteine originally present. As mentioned above, the same procedure works for cysteine; it is also possible to run an assay for homocysteine and cysteine (or any other amino acid) concurrently as long as each has its own appropriate internal standard.

The internal reference standard is any suitable compound which will behave identically with the endogenous target compound throughout the procedure up to analysis on the mass spectrometer, but which is distinguishable under mass spectrometric analysis and can be separately measured. Examples of suitable internal references are deuterated or tritiated analogs of the target amino acid to be measured, or deuterated or tritiated compounds sufficiently similar to the target amino acid to be effectively identical for the purposes of this assay, or other analogs of the target amino acid containing sufficient amounts of $C^{13}$ or $N^{15}$ or other stable isotope markers. Thus the labelled reference compound is indistinguishable from the unlabelled target during handling but will provide different and distinct ions for quantification on the mass spec. Examples of preferred compounds for this assay are, deuterated forms of cysteine, e.g. D,L-[3,3,3',3'-$^2$H$_4$]cystine and deuterated homocysteine, e.g. D,L-[3,3,3',3',4,4,4',4'-$^2$H$_8$]homocysteine. Compounds suitable for use as internal standards are available from, e.g. Merck Sharp & Dohme.

Quantification is based on the assumption that the ratio of measured target compound to measured internal standard is the same as the ratio of the total unknown amount of target compound in the initial sample was to the total amount of added internal standard. This assumes the same recovery rate for both the target and the internal standard. In the case of sulfhydryl compounds, recovery depends at least partially on the various possible forms free and complexed, that the sulfhydryl amino acids can take. Accordingly, for each assay it is crucial that the relative ratio of target and internal standard in the free state and in each possible complexed state be the same; this assures that the same relative percent of target and internal standard will be lost (and recovered). Therefore a reducing agent is added to the initial sample containing both the target and the internal standard; sufficient reducing compound is added to cleave all the disulfide bridges so that all the sulfhydryl amino acids are in their free state. A compound which will prevent rejoining of the disulfide bridges can be added, e.g. iodoacetate, iodoacetamide, or iodopropane, to insure that all sulfhydryl amino acids will remain in the free form. Alternatively, the compounds are allowed to reform disulfide bridges at will, with the assumption that the target and standard sulfhydryl amino acids will form identical types and numbers of such complexes, so that there is the same ratio for the amount of target and internal standard sulfhydryl amino acid in the free state, in each possible complex, and in the amounts of target and internal standard measured by the mass spectrometer, as was in the original sample. Suitable reducing agents are those capable of breaking the disulfide bonds without destroying the remainder of the molecule, e.g., 2-mercaptoethanol, dithiothreitol, and sodium borohydride.

Optionally, it may be necessary or desirable to partially purify the target amino acid and the internal standard either before or after the addition of the reducing agent. Any means known for the purification and separation of amino acids, e.g. filtration, column chromatography, anion and/or cation exchange chromatography, gas chromatography, liquid chromatography, high pressure liquid chromatography, molecular sieving, etc., may be used. Methods of selecting suitable separation and purification techniques, and means of carrying them out, are known in the art. See, e.g., Labadarios, D., I. M. Moodie, and G. S. Shephard, J. Chrom. 310:223–231 (1984) and references cited therein; Shahrokhi, F., and C. W. Gehrke, J. Chrom. 36:31–41(1968).

Optionally, it also may be necessary or desirable to modify the target compound and the internal standard to alter or improve certain characteristics to facilitate purification and/or separation. This practice is well-known in the art as derivatization. For example, it may be desired to convert the target and reference compounds to analogs having improved solubility, different charge, increased volatility, etc., to facilitate purification and/or separation before analysis on the mass spectrometer. See, e.g., Knapp, D. R., *Handbook of Analyti-* cal *Derivatization Reactions* (John Wiley & Sons, New York, 1979). A preferred procedure involves converting the target and reference compounds to their silyl derivatives to facilitate separation and identification on a combined gas chromatograph/mass spectrometer apparatus. Means and methods of silating compounds for this purpose are known in the art, see, e.g., Knapp, supra; Bierman, C. J., C. M. Kinoshita, J. A. Marlett, and R. D. Steele, J. Chrom. 357:330–334(1986). A preferred method involves combining the target compound with the internal reference, adding reducing agent to effect randomization, partially purifying the resulting mixture of free and complexed sulfhydryl amino acids, dissolving the product in acetonitrile and adding N-methyl-N-(t-butyldimethylsilyl)trifluoroacetamide to achieve silation. The resulting silated sulfhydryl target and reference compounds are then concentrated to provide the sample injected into the GC/mass spectrometer.

Using this procedure on serum, it is possible to achieve sensitivities of about 1 μmol/liter for total homocysteine and the assay is linear over the range of 1-1000 μmol/liter for total homocysteine. The normal range for homocysteine in human serum is from about 7 to about 22 μmol/liter, and in human urine is from about 1 to about 20 μmol/liter. Homocysteine levels above these ranges are indicative of cobalamin and/or folate deficiency; the higher the level, the stronger the indication.

It has also been discovered that by running a second assay, for methylmalonic acid (MMA) levels, either concurrently with the assay for homocysteine or subsequently thereto, it is possible to distinguish between cobalamin and folic acid deficiency. While both cobalamin and folic acid deficiency will raise homocysteine levels, cobalamin deficiency will usually raise methylmalonic acid levels while folate deficiency usually will not. When homocysteine levels are elevated in individuals without inherited defects, at least one of folate or cobalamin is deficient. When MMA is also elevated, cobalamin is usually deficient. Accordingly, when both homocysteine and MMA are elevated, it is likely that cobalamin is deficient (otherwise MMA would be normal) but it is not clear whether or not folate is also deficient (since any contribution by folate deficiency to the total homocysteine elevation may be masked by the effect of the cobalamin deficiency). Conversely, when homocysteine is high but MMA is normal, the elevated homocysteine is likely to be due to folate deficiency since if it were due to cobalamin deficiency, MMA would usually also be high. It is possible in some cases that MMA levels will be elevated due to cobalamin deficiency even before homocysteine levels begin to rise or that homocysteine will be elevated due to cobalamin deficiency before MMA levels begin to rise. The information supplied by this assay is thus a valuable adjunct to early proper diagnosis of these deficiencies.

In this combined homocysteine/MMA assay, homocysteine levels are suitably assayed by any of the means given above. The procedure of the present invention is preferred. The MMA is suitably assayed by the methods of, e.g., Norman, E. J., O. J. Martelo, and M. D. Denton, Blood 59(6):1128 (1982) or Marcell, P. D., S. P. Stabler, E. R. Podell, and R. H. Allen, Anal. Biochem. 150:58–66 (1985). Preferably, the sample is combined with an internal reference standard comprising a known amount of methylmalonic acid labelled with a stable isotope marker, preferably a deuterated analog of MMA. The amount of labelled and unlabelled MMA present is then measured on a mass spectrophotometer and the amount of MMA in the original sample is calculated from the known amount of labelled MMA originally added. As with homocysteine, the labelled and unlabelled MMA may be subjected to partial purification and/or derivatization before analysis on the mass spectrometer. The preferred derivates are silyl analogs; analogs of N-methyl-N(t-butyldimethylsilyl)trifluoroacetamide are particularly preferred.

It is also possible to measure one or more non-sulfhydryl amino acids, e.g. methionine, concurrently with homocysteine, MMA, or both, provided the appropriate internal standards are included. A suitable internal standard for the non-sulfhydryl amino acids is norleucine or a suitably labelled analog of the non-sulfhydryl amino acid.

Once folate and/or cobalamin deficiency has been determined, the progress of treatment can be monitored by repeating the assays periodically during and after treatment. A drop in the level of homocysteine in the serum and/or urine after oral or parenteral administration of cobalamin and/or folate as the case may be, confirms the diagnosis.

A further understanding of this invention can be had from the following non-limiting examples. As used hereinabove and below unless expressly stated to the contrary, all temperatures and temperature ranges refer to the centigrade system and the terms ambient and room temperature refer to about 20°–25° C. The term percent or (%) refers to weight percent and the terms mole and moles refer to gram moles.

EXAMPLE I

Correlation Between Various Clinical Indices and Cobalamin Deficiency

Over a 24 month period (between September, 1983 and September, 1985) we measured serum cobalamin levels in 7,747 patients in response to requests for this test from physicians at two New York City Hospitals (Columbia-Presbyterian Medical Center and Harlem Hospital Center). Of this group, 301 patients had serum levels below 200 pg/ml the lower limit of normal as stated by the manufacturer of the "improved" radioassay kit using purified intrinsic factor (BioRad Laboratories, Richmond, Calif.). In order to determine how many of the patients with low serum cobalamin levels were truly deficient in the vitamin, we attempted to study every patient thoroughly. As often as was possible, we obtained a full clinical (including neurological) evaluation, blood and bone marrow smears, Schilling tests and serum tests for antibodies to intrinsic factor, and then observed the response of the patient to a course of treatment with cyano-cobalamin.

We were able to reach a firm conclusion as to whether or not cobalamin deficiency was present in 138 of the 301 patients. In 79 of the 138, a clinical or hematologic syndrome, or both, was present that clearly responded to cyano-cobalamin treatment. These patients were considered to be deficient. An analysis of the clinical presentation of these deficient patients showed a number of surprising findings, in that many did not have the classical hallmark findings of megaloblastic anemia due to cobalamin deficiency. The hematocrit was normal (i.e., anemia was not present) in 34 (43%), nearly half of the patients. Moderately severe anemia (Hct <24% or hemoglobin <8 g/dl) was only present in 16

(or one-fifth) of the 79 patients. In 36 patients (45.6%), there were no symptoms present that could be attributed to cobalamin deficiency. The white blood count was normal in 85%; the platelet count was normal in 76%; the serum bilirubin was normal in 74%; and the serum lactate dehydrogenase (LDH) was normal in 40%. Therefore these laboratory findings, which are thought to be typical of patients with megaloblastic anemia, were often or usually missing in the deficient group. Also, the serum cobalamin was >100 pg/ml in 23 (or 29%) of the deficient patients, indicating that the degree of depression of the serum cobalamin also could not be reliably used to predict accurately whether a patient was deficient. Even an elevated MCV, thought to be so characteristic of cobalamin deficiency, was not seen in 15 (19%) of the deficient patients. In those patients with a high MCV, the degree of elevation of the MCV was often slight: 28 (or 35%) of the 79 patients had MCV's in the 100–110 fl range. Thus, only 36 patients (or 46%) had a markedly elevated MCV (>110 fl).

Among the 138 patients about whom we were able to reach a firm conclusion, there were 59 who clearly showed no response in any way to cyano-cobalamin treatment. These patients were considered not deficient. In this not-deficient group, 13 (or 22%) of the 59 had an elevated MCV, and 6 (or 10%) had a serum cobalamin below 100 pg/ml, a further indication that the MCV or the degree of depression of the serum cobalamin could not be used as reliable indicators of whether patients were deficient in cobalamin.

After we discovered that a substantial number of the deficient patients had only slightly low serum cobalamin levels, i.e., in the 100–200 pg/ml range, we undertook a review of all patients with serum cobalamin levels in the 200 to 300 pg/ml range (low normal). In this way, we discovered several patients that were clearly deficient in cobalamin that had serum cobalamin levels >200 pg/ml.

These findings led us to conclude that large numbers of patients with cobalamin deficiency lack the "typical" clinical and hematologic features usually expected to be present in cobalamin deficiency and that there is clearly a need for new tests that would help establish whether deficiency was indeed present.

We then measured serum levels of homocysteine and methylmalonic acid in the specimens from the 79 deficient and the 59 non-deficient patients. Levels of both homocysteine and methylmalonic acid were clearly elevated (homocysteine, above 30 uM and methylmalonic acid, above 150 ng/ml) in 60 (76%) of the 79 deficient patients. The homocysteine level was clearly elevated (without clear elevation of the methylmalonic acid level) in 10 (13%) of the 79, and the methylmalonic acid level was clearly elevated (without clear elevation of the homocysteine level) in 4 (5%) of the patients. In the remaining 5 of the 79 deficient patients (6%), neither test was clearly elevated.

In contrast, in the 59 not deficient patients, both tests were clearly elevated in 1 patient (2%); only the homocysteine was clearly elevated in 6 (10%); and only the methylmalonic acid level was clearly elevated in 9 (15%). In the remaining 43 patients (73%), neither test was clearly elevated. Even in the minority of the non-deficient patients in whom one or both tests was clearly elevated, the tests proved diagnostically useful. Eleven of the 16 patients with clear elevations of one or both tests proved to have underlying disorders of cobalamin absorption, such as pernicious anemia, severe atrophic gastritis and ileal disease, with the potential to cause cobalamin deficiency at some later time. Such patients need to receive prophylactic cyanocobalamin treatment. An additional 2 patients of the 16 had underlying folic acid deficiency to explain the elevation of serum homocysteine.

These tests also appear to be useful in the diagnosis of folate deficiency. In 120 consecutively studied alcoholic patients with anemia, bone marrow examinations were done. In 38 patients the bone marrow smear was megaloblastic. After one patient who had cobalamin deficiency was excluded from the analysis, the remaining 37 patients were considered highly likely to have folic acid deficiency. The serum folate concentration (the most widely used diagnostic test for folate deficiency) was low in only 15 of the 37 patients (41%), whereas the serum homocysteine was clearly elevated in 27 (73%) of the 37 patients. Thus, the serum homocysteine was found to be a more sensitive test for detecting folate deficiency than the serum folate concentration. In 15 patients with megaloblastic bone marrows in whom the red cell folate concentration (RCF) was measured, the RCF was low in 10 of the 15 (67%) and the serum homocysteine was clearly elevated in 13 (87%). Thus, the serum homocysteine assay also was more sensitive than the red cell folate assay.

EXAMPLE II

Representative Preferred Procedure for Measuring Homocysteine in Human Serum

Human blood serum is combined with a suitable internal reference standard, e.g. D,L-[3,3,3',3',4,4,4',4'-$^2$H$^8$]homocystine, now available from Merck Sharp and Dohme Isotopes (Montreal, Canada) and mixed well.

Excess reducing reagent (e.g. 2-mercaptoethanol, dithiothreitol, or sodium borohydride) is then added to insure that all the homocysteine is reduced to the free form. A chelating agent such as EDTA or EGTA may optionally be added to remove any metal ions which may otherwise bind to the free sulfhydryl group. The reaction mixture is stirred and optionally heated at about 25° to about 150° C. for about 1 min to about 60 min to insure complete randomization of the labelled and unlabelled homocysteine.

Protein is then removed by, e.g., heat denaturation, ion exchange chromatography, gel filtration, or preferably by addition of a compound which precipitates proteins, e.g. sulfosalicylic acid, picric acid, ammonium sulfate, etc. The resulting mixture is stirred and centrifuged to remove protein precipitate. If not already acidic, the supernatant is acidified and added to a cation exchange column, e.g. BioRad AG 50W-X8 (200–400 mesh), hydrogen form (BioRad Laboratories, Richmond, Calif.), to remove any negatively charged salts. The amino acids are then eluted, adjusted to a basic pH, and added to an anion exchange column, e.g. BioRad AG1-X8 (100–200 mesh), acetate form, to remove any positive salts. The amino acids are then eluted, dried, and transferred to small sealable vials, preferably with Teflon-lined septum caps. N-methyl-N-(t-butyldimethylsilyl)trifluoroacetamide in acetonitrile is then added, the vials are sealed and left at about 20° to about 150° C. for about 5 min to about overnight, to complete the silation reaction. Preferably, the vials are left at room temperature overnight, or heated at about 80° C. for about 1 hour. Excess derivatizing agent may then be removed by addition of water (which hydrolyzes the derivatizing agent) and any volatile solvent. The mixture is centrifuged to clear the emulsion and the non-aqueous layer, which contains most of the derivatized compound, is transferred to a clean vial and evaporated almost to dryness, e.g. under nitrogen, to reduce the volume.

The resulting preparation is then injected onto a gas chromatograph/mass spectrophotometer with an injection port temperature of from about room temperature to about 350° C. and a column head of about 5 to about 45 psi. The capillary column is run at about 20° to about 250° C. for about 1 to about 15 min. Thereafter the temperature is raised to about 75° to about 350° C. at about 1° to about 30° C./min. The exact time and temperature at which the homocysteine elutes is determined by first running a known amount of homocysteine. Thereafter the sample is run and data collected in the scanning mode or preferably in the selected ion monitoring mode.

EXAMPLE III

Representative Specific Procedure for Measuring Homocysteine in Human Serum

L-homocysteine and L-cysteine were purchased from Sigma Chemical Co. (St. Louis, Mo.); L-methionine, other amino acids, and N-methyl-N-[t-butyldimethylsilyl]trifluoroacetamide were obtained from Pierce Chemical Co. (Rockford, Ill.); D,L-[3,3,3',3',-4,4,4'4'-$^2H_8$]homocystine (98.4%) was obtained by a custom synthesis from Merck, Sharp and Dohme Isotopes (Montreal, Can.); and D,L-[3,3,3',3'-$^2H^4$]cystine (98%) and L-[methyl-$^2H_3$]methionine (98%) were purchased from Cambridge Isotope Laboratories (Woburn, Mass.) Blood samples were obtained from normal healthy blood donors at the Belle Bonfils Blood Bank, Denver, Colo., at the time of blood donation. Consecutive blood donors were chosen such that samples were obtained from five males and five females in each of the following age groups: 18–26, 27–35, 36–45, 46–55, and 56–65 (for a total of fifty samples). The samples were obtained between 9 a.m. and 1 p.m., were allowed to clot at room temperature for 1 to 4 hours, centrifuged at 1500×g for 30 min, and the serum was removed and stored at −20° C. Other samples were obtained from laboratory personnel. They were allowed to clot at room temperature for 0 to 24 hours before centrifugation at 4° C., or were added to heparin or EDTA and allowed to stand at room temperature for 0 to 24 hours before the plasma was collected by centrifugation at 4° C. Sprague-Dawley rats, 250–350 g, were obtained from SASCO, Inc. (Omaha, Nebr.) and blood was obtained by intracardiac puncture under ether anesthesia. Serum was collected and stored as described above for the human blood donor samples.

A volume of 50 μl of $H_2O$ containing 5 nmol of D,L-[3,3,4',4',4,4,4',4'-$^2H_8$]homocystine, 25 nmol of D,L-[3,3,3',3'-$^2H_4$]cystine, and 15 nmol of L-[methyl$^2H_3$-]methionine was added to 100 μl of serum. After mixing, 2.5 ml of $H_2O$ containing 158 μg of $Na_2EDTA$ and 100 μl of 2-mercaptoethanol were added followed by mixing and boiling at 100° C. for 15 min. After cooling to room temperature, 100 μl of $H_2O$ containing 25 μg of sulfosalicylic acid, and 25 μl of 6N HCl were added followed by mixing and centrifugation at 1000×g for 15 min. The supernatant was then applied to disposable columns containing 200 μl of the cation exchange resin AG 50W-X8 (200–400 mesh), hydrogen form (BioRad Laboratories, Richmond, Calif.), which had been preequilibrated with $H_2O$. After washing with 6 ml of $H_2O$, the amino acids were eluted with 2 ml of 8N $NH_4OH$. The eluates were applied directly to disposable columns containing 200 μl of the anion exchange resin AG1-X8 (100–200 mesh), acetate form (BioRad Laboratories, Richmond, Calif.), which had been washed and equilibrated with $H_2O$. After washing with 9 ml of $H_2O$, the amino acids were eluted in 2 ml of 0.1 ml HCl and taken to dryness in a Speed Vac vacuum concentrator (Savant Instruments, Inc., Hicksville, N.Y.). The dried samples were then dissolved in 250 μl of $H_2O$, transferred to 300 μl Reacti-vials (Pierce Chemical Co., Rockford, Ill.) and taken to dryness in the vacuum concentrator.

The t-butyldimethylsilyl derivatives of the amino acids were prepared by adding 10 μl of acetonitrile and 10 μl of N-methyl-N-(t-butyldimethylsilyl)trifluoroacetamide to each vial, sealing them with Teflon-lined septum caps, and allowing them to stand at room temperature (22° C.) overnight or heating them to 80° C. for 1 hour. Hexane, 100 μl, was added, and after vortexing for 10 sec, $H_2O$, 20 μl, was added to hydrolyze any unreacted derivatizing agent. After vortexing for an additional 10 sec, the samples were centrifuged at 1000×g for 5 min, and the upper hexane layer was decanted, transferred to microcentrifuge tubes, and dried to approximately 10 μl by applying a stream of nitrogen. Care was taken to avoid complete dryness, since this results in a major loss of the derivatives. Approximately 2 μl was injected onto the capillary column via the falling-needle injector.

Sample analysis was performed on a Hewlett-Packard (Palo Alto, Calif.) 5992B gas chromatograph-mass spectrophotometer equipped with a 9825B calculator, a 9876A printer, and a molecular jet separator. The injection port was modified to accept a falling-needle injector, and an auxiliary make-up carrier gas line was supplied to the jet separator. Sample resolution was achieved on a Durabond DB-1 fused silica capillary column (30 m×0.25 mm i.d., 0.25 um film thickness) from J & W Scientific, Inc. (Rancho Cordova, Calif.).

The gas chromatograph-mass spectrophotometer was operated under standard autotune conditions with an injection port temperature of 250° C. and a column head pressure of 26 psi. The capillary column was equilibrated at 180° C., and 1 min after sample injection was increased to 276° C. at 8° C./min. Data were collected from 4.8 to 9.6 min using the selected ion monitoring mode. The following [M-57]+ ions were monitored using a 50 msec dwell time for each: homocysteine monomer, m/z 420.2;[3,3,4,4-$^2H_4$]homocysteine monomer, m/z 424.2; cysteine monomer, m/z 406.2; [3,3-$^2H_2$]cysteine monomer, m/z 408.2; methionine, m/z 320.2; and [methyl-$^2H_3$]methionine, m/z 323.2. Total homocysteine was quantitated by dividing the integrated area of the m/z 420.2 peak that eluted at approximately 8.9 min (the exact times were determined daily with standards) by the integrated area of the m/z 424.2 peak that eluted at the same time, and then multiplying by 100 umol/liter, which is the equivalent amount of [3,3,4,4-$^2H_4$]homocysteine monomer that was added to each sample. Total cysteine was quantitated in the same manner utilizing the m/z 406.2 and m/z 408.2 peaks that eluted at approximately 7.7 min and multiplying their ratio by 500 umol/liter, which is the equivalent amount of the [3,3-$^2H_2$]cysteine monomer added to the samples.

Methionine was quantitated in the same manner utilizing the m/z 320.2 and m/z 323.2 peaks that eluted at approximately 5.4 min and multiplying their ratio by 150 μmol/liter, which is the amount of [methyl-$^2H_3$]methionine added to the samples. The integrated areas for the three internal standard peaks, i.e. the m/z 424.2, m/z 408.2, and m/z 323.2 peaks eluting at about 8.9, 7.7, and 5.4 min, respectively, were corrected for the amounts contributed to them by endogenous total homocysteine, endogenous total cysteine, and endogenous methionine as a result of naturally occurring isotope abundance. These corrections, which were determined with unenriched homocysteine, cysteine, and methionine on a daily basis were as follows: (i)approximately 1.5% of the area of the m/z 420.2 peak at 8.9 min was present as a m/z 424.2 peak at 8.9 min, (ii) approximately 21.4% of the area of the m/z 406.2 leak at 7.7 min was present as a m/z 408.2 peak at 7.7 min, and (iii) approximately 3.1% of the area of the m/z 320.2 peak at 5.4 min was present as a m/z 323.2 peak at 5.4 min.

In experiments in which cysteine-2-mercaptoethanol, homocysteine-2-mercaptoethanol, cystine, homocysteine-cysteine dimer, and homocystine were detected and monitored, the run time was extended to 20 min and the final temperature was increased to 335° C. Spectra for cystine and homocystine were obtained by derivatizing these compounds directly without employing the standard reduction with 2-mercaptoethanol. Spectra for cysteine-2-mercaptoethanol and homocysteine-2-mercaptoethanol were obtained from cystine and homocystine, respectively, in experiments in which these compounds were reduced with-2-mercaptoethanol before derivatization. This latter technique was used to obtain spectra for homocysteine-cysteine dimer except that an equal mixture of homocystine and cystine was reduced by 2-mercaptoethanol followed by derivatization. The sensitivities of the assays were measured by determining, e.g., the ratio of homocysteine monomer to [3,3,4,4-$^2H_4$] homocysteine monomer, at which the standard curves deviate from linearity as described by Zinn, A. B., D. G. Hine, M. J. Mahoney, and K. Tanaka, Pediatr. Res. 16:740–745(1982).

The urinary clearances of total homocysteine, methionine, and total cysteine were determined with the following equation as illustrated for total homocysteine: total homocysteine/creatinine clearance ratio=100-×[urine total homocysteine (umol/L)/urine creatinine(umol/L)]/[serum total homocysteine (umol/L)/serum creatinine (umol/L)]

The extensive nature of the partial sample purification utilized in this procedure was necessary because of the complex mixture of amino acids and other organic compounds present in serum and urine, and because of the relatively low concentrations of total homocysteine present. Experiments in which known amounts of [methyl-$^{14}C$]methionine or [$U^{14}C$]cystine were added to serum and urine samples showed that approximately 70% of the radioactivity from both amino acids was recovered in the final hexane solution at the end of the extensive partial purification and derivatization procedures. Similar recovery studies were not performed for homocystine because radiolabelled homocystine is not commercially available.

The structure and m/z value of the t-butyldimethylsilyl derivative of homocysteine is shown below together with some of the fragmentation positions and the m/z values of the corresponding fragments at $[M]^+$, $[M-15]^+$, $[M-57]^+$, and $[M-159]^+$:

$$\begin{array}{c}
CH_3 \\
| \\
CH_3-C-CH_3 \\
| \\
CH_3-Si-CH_3 \\
\end{array}$$

$$CH_3-\overset{CH_3}{\underset{CH_3}{\overset{|}{\underset{|}{C}}}}-\overset{CH_3}{\underset{CH_3}{\overset{|}{\underset{|}{Si}}}}-S-CH_2-CH_2-\overset{NH}{\underset{H}{\overset{|}{\underset{|}{C}}}}-\overset{O}{\overset{||}{C}}-O-\overset{CH_3}{\underset{CH_3}{\overset{|}{\underset{|}{Si}}}}-\overset{CH_3}{\underset{CH_3}{\overset{|}{\underset{|}{C}}}}-CH_3$$

| | |
|---|---|
| $[m-159]^+ = 318$ | |
| $[m-57]^+ = 420$ | |
| $[m-15]^+ = 462$ | |
| $[m]^+ = 477$ | |

The molecular weights of homocysteine monomer, cysteine monomer, homocystine, cystine, homocysteine-2-mercaptoethanol, cysteine-2-mercaptoethanol, homocysteine-cysteine dimer, and methionine are shown in FIG. 1 together with the mass spectra of their t-butyldimethylsilyl derivatives. The molecular weight of a particular derivative is equal to the molecular weight of the amino acid or disulfide, plus 114 for each t-butyldimethylsilyl group that is bound to each available —COOH, —$NH_2$, —SH, and —OH group. In the case of homocysteine monomer, cysteine monomer, homocysteine-2-mercaptoethanol, cysteine-2-mercaptoethanol, and methionine, a major peak was present at $[M-57]^+$. In the case of homocystine, cystine, and homocysteine dimer, the major peak was at $[M/2]^+$. A $[M-57]^+$ peak was not observed with homocystine and only small $[M-57]^+$ peaks were observed for cystine and homocysteine-cysteine dimer.

Figure 3:
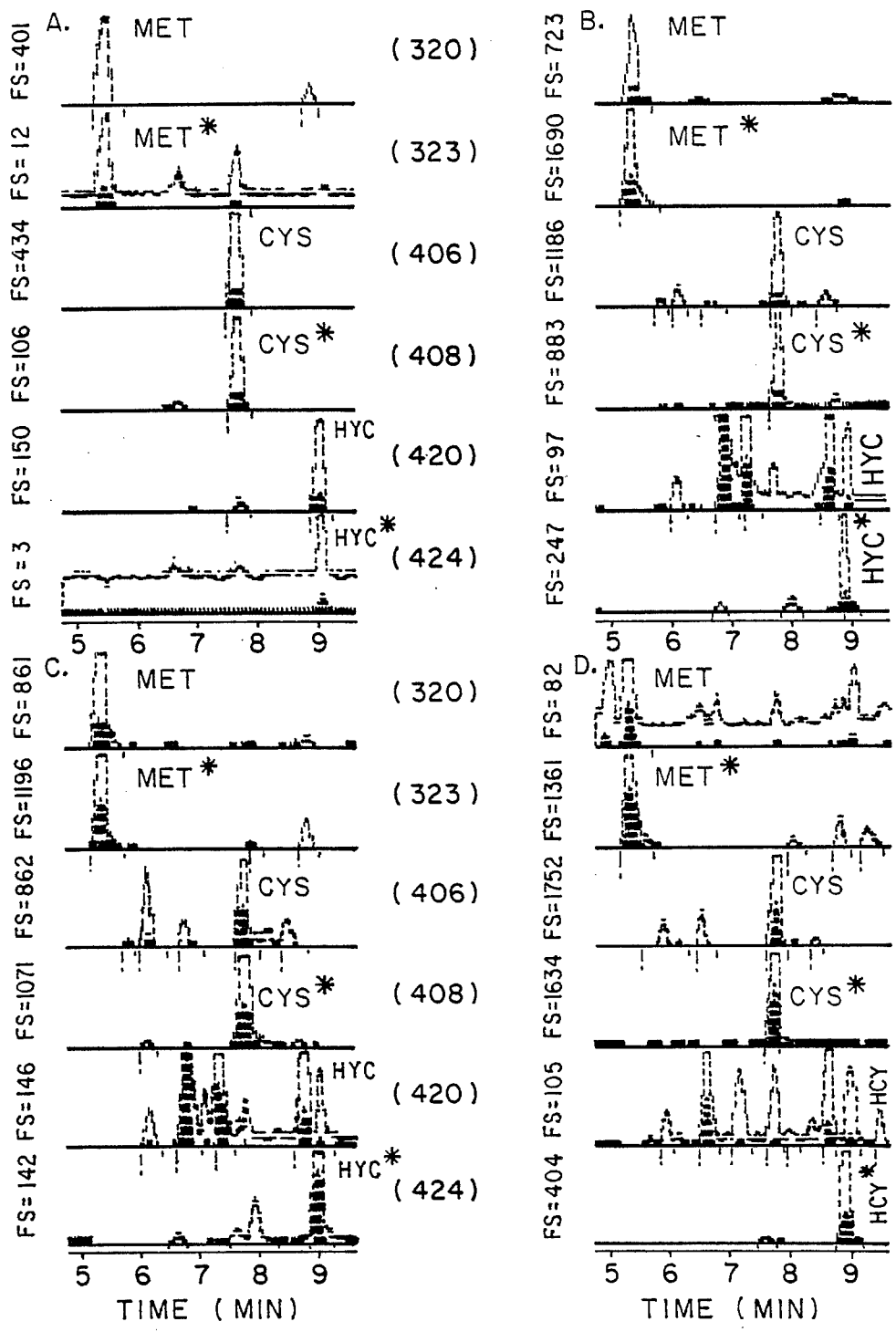
FIGS. 3A, B, C and D illustrate the chromatograms of the t-butyldimethylsilyl derivatives of amino acids.

FIG. 3 shows chromatograms of the t-butyldimethylsilyl derivatives of amino acids obtained after reduction from (A) a mixture containing methionine, cysteine, and homocysteine in a ratio of 1:3:1; (B) 100 μl of normal human serum; (C) 100 μl of normal rat serum; and (D) 100 μl of normal human urine. The amino acids studied were: methionine (MET); cysteine monomer (CYS); homocysteine monomer (HCYS); [methyl-$^2H_3$]methionine (MET*); [3,3-$^2H_2$]cysteine monomer (CYS*); and [3,3,4,4-$^2H_4$]homocysteine monomer (HCYS*). MET*, CYS*, and HCYS* were not added to sample A and the peaks bearing their designation represent the amounts contributed to them by MET, CYS, and HCYS, respectively, as a result of naturally occurring isotope abundance. Numbers in parentheses represent the values for m/z that were scanned by selected ion monitoring. The values for "F.S." are relative values for the full scale of the heavy-dashed tracing; the light-dashed tracing is a 10X attenuation. The values determined for endogenous total homocysteine were 18.9, 6.5, and 3.6 μmol/L for B, C, and D, respectively. The values determined for endogenous total cysteine were 369, 173, and 238 μmol/L for B, C, and D, respectively. The values determined for endogenous methionine were 16.8, 60.4, and 3.2 μmol/L for B, C, and D, respectively. FIG. 3A demonstrates that the capillary column gives a complete separation for these three amino acids. The elution profiles of cysteine-2-mercaptoethanol, homocysteine-2-mercaptoethanol, cystine, homocysteine-cysteine, and homocystine are not shown, but they were also present and eluted as single symmetrical peaks with respective elution times of 11.8, 12.9, 16.3, 17.4, and 18.4 min.

Studies with samples of human serum and urine, and rat serum, in which $[3,3,3',3',4,4,4',4'-^2H_8]$homocystine, $[3,3,3',3'-^2H_4]$cystine and [methyl-$^2H_3$]methionine were not added, demonstrated that substances that might interfere with their use as internal standards for quantitation were not present. The sensitivities of the assays were 1 μmol/L for total homocysteine, 5 μmol/L for total cysteine, and 2 μmol/L for methionine under the standard conditions that used 50 μmol/L of $[3,3,3',3',4,4,4',4'-^2H_8]$homocystine, 250 μmol/L of $[3,3,3',3'-^2H_4]$cystine, and 150 μmol/L of [methyl-$^2H_3$]methionine, although the sensitivities could be improved in each case by decreasing the amounts of internal standards added. Assays performed under standard conditions showed that the assays for each of the three amino acids were linear over the ranges of 1 to 1000 μmol/L for total homocysteine, 5 to 5000 μmol/L for total cysteine, and 2 to 2000 μmol/L for methionine.

A chromatogram obtained with 100 μl of normal human serum is shown in FIG. 3B. Endogenous total cysteine is present in the largest amount followed by endogenous methionine and then endogenous total homocysteine. Approximately 70% of the total cysteine was present in the cysteine monomer peak at approximately 7.7 min with the remaining 30% being present (data not shown) as cysteine-2-mercaptoethanol (20%), cystine (9%), and the homocysteine-cysteine dimer (1%) peaks which eluted at later time periods (see above). Approximately 60% of the total homocysteine was present in the homocysteine monomer peak that eluted at approximately 8.9 min with the remainder being present (data not shown) in the homocysteine-2-mercaptoethanol (25%), homocysteine-cysteine dimer (14%), and the homocystine (1%) peaks that eluted later (see above).

The percentages of the various forms of cysteine and homocysteine varied considerably from sample to sample but for a given sample were not altered when the period of boiling with 2-mercaptoethanol was varied from 1 to 60 min or when the amount of 2-mercaptoethanol was varied from 5 to 100 μl. The ratio of endogenous cysteine to [3,3-$^2H_2$]cysteine was essentially identical in all of the various peaks containing cysteine. The ratio of endogenous homocysteine to [3,3,4,4-$^2H_4$]homocysteine was essentially identical in all of the various peaks containing homocysteine. These observations indicate that the endogenous and internal standard forms of cysteine and homocysteine are completely reduced and released from their various disulfide forms, including the forms bound to protein, by the initial 15-min reduction with 100 μl of 2-mercaptoethanol, and that minor but significant amounts of various disulfides are reformed at subsequent stages in the purification and derivatization procedures. This subsequent partial disulfide reformation does not prevent or hinder the quantitation of endogenous total cysteine and endogenous total homocysteine, however, because the internal standards utilized for cysteine and homocysteine, i.e. $[3,3,3',3'-^2H_4]$cystine and $[3,3,3',3',4,4,4',4'-^2H_8]$homocystine, are also completely reduced and then participate in the partial disulfide reformation to the same extent as endogenous total cysteine and endogenous total homocysteine. It is possible to quantitate endogenous total cysteine using the ratio of deuterated cysteine to endogenous cysteine in any of the cysteine monomer, cysteine-2-mercaptoethanol, cystine, or homocysteine-cysteine dimer peaks since the values for this ratio are the same in all four peaks for any given sample. It is also possible to quantitate endogenous total homocysteine using the ratio of deuterated homocysteine to endogenous homocysteine in any of the homocysteine monomer, homocysteine-2-mercaptoethanol, homocystine or homocysteine-cysteine dimer peaks since the values for this ratio are the same in all four peaks for any given sample. We have chosen to measure and use the ratios obtained in the cysteine monomer and homocysteine monomer peaks in our standard procedure because they are usually the largest peaks and because they elute earlier than the other peaks.

Preliminary studies indicate that it is possible to couple iodoacetamide to cysteine monomer and homocysteine monomer after the initial reduction step and then proceed with the purification and derivatization procedures in the standard way (data not shown). This modification, which prevents the reformation of disulfides, has not been evaluated in detail, however.

When the reduction with 2-mercaptoethanol is omitted from the standard procedure with human serum, cystine, homocystine, and homocysteine-cysteine dimer peaks are observed that contain endogenous forms of cysteine, homocysteine and both homocysteine and cysteine, respectively. Cysteine-2-mercaptoethanol and homocysteine-2-mercaptoethanol are not detectable under these conditions (data not presented).

Figure 2:
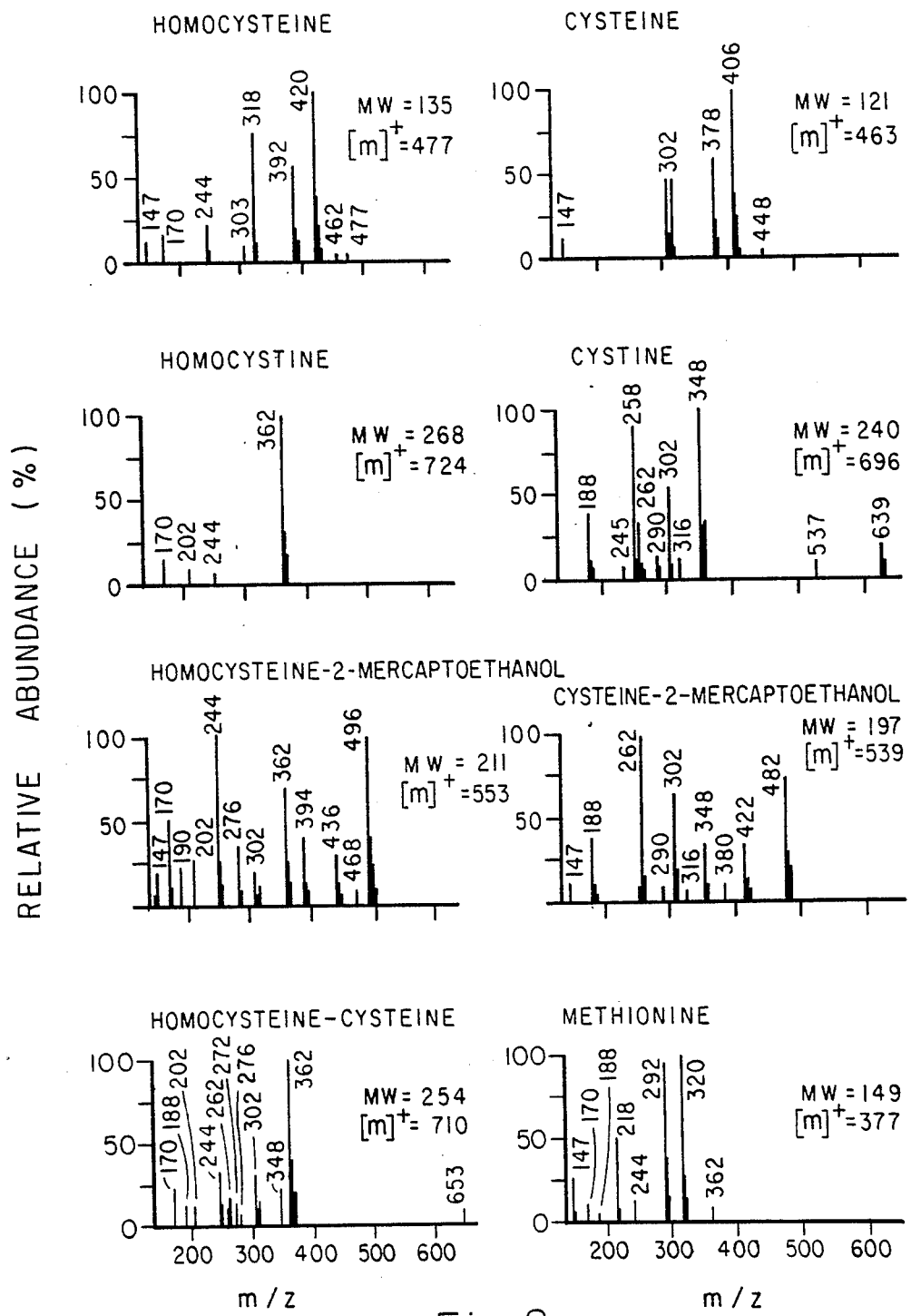
FIG. 2 illustrates the mass spectra of sulfhydryl amino acids.

Chromatograms obtained with 100 μl of normal rat serum and 100 μl of normal human urine are shown in FIGS. 2C and 2D, respectively, and are similar to the chromatogram obtained with normal human serum (FIG. 2B).

Studies performed with a single sample of pooled normal human serum that was repeatedly frozen and thawed, and assayed on 16 different occasions over a one-month period gave values for the coefficient of variation of 19.7%, 17.4% and 5.6% for the assay of total homocysteine, total cysteine, and methionine, respectively. No significant change or trend in the values for these three amino acids was observed over the one-month period nor have changes been observed when the same serum was assayed on other occasions over a 12-month period.

Values for serum total homocysteine obtained with blood samples that were drawn and immediately centrifuged at 4° C. were the same (10% difference) as those obtained with portions of the same blood samples that were incubated at room temperature for 1 hour prior to centrifugation, but increased by approximately 35% and 75% when the incubation was prolonged for 4 hours and 24 hours, respectively, prior to centrifugation. Values for serum total cysteine were unchanged over the 24 hour incubation period. Values for serum methionine were unchanged at 1 hour and increased by 10% and 25% at 4 h and 24 h, respectively. Plasma collected in EDTA or heparin gave values that were the same as those for serum for all three amino acids at all time periods except in the case of methionine where the values for both types of plasma did not increase at all over the 4 h or 24 h incubation periods. Incubation studies performed with rat serum gave results similar to those obtained with human serum. Values for urine total homocysteine, total cysteine, and total methionine were unchanged when urine samples were incubated at room temperature for 0 h to 24 h.

The values for the actual mean ($\mu$mol/L) and range obtained for total homocysteine, total cysteine, and methionine in serum samples from 50 normal human subjects and 50 normal rats, calculated as the mean $\pm 2$ S.D. after log transformation to correct for skewness towards higher values were: human serum total homocysteine, 13.0 (7.2–21.7); human serum methionine, 25.5 (13.7–43.5); human serum total cysteine, 261 (174–378); rat serum total homocysteine, 5.6 (3.2–9.6); rat serum methionine, 56 (39–83); and rat serum total cysteine, 190 (131–283). The values for the actual mean ($\mu$mol/L or $\mu$mol/10 mmol creatinine) and range obtained for urine samples from the same 50 normal human subjects, calculated as defined above, were: human urine total homocysteine, 7.2 (1.4–24.7); human urine total homocysteine /10 mmol urine creatinine, 11.2 (2.0–36.7); human urine methionine, 5.9 (0.4–35.1); human urine methionine/10 mmol creatinine, 6.3 (1.5–19.1); human urine total cysteine, 260 (68–729); human urine total cysteine/10 mmol creatinine, 344 (158–655). The normal ranges for total cysteine and methionine in urine are tighter when expressed as $\mu$mol/10 mmol creatinine than when expressed as $\mu$mol/L.

Values for total homocysteine and total cysteine were significantly ($P<0.05$) higher in human serum than in rat serum. Values for methionine were significantly ($P<0.05$) higher in rat serum than in human serum.

Human serum total homocysteine, total cysteine, and methionine were not correlated significantly with urine total homocysteine, total cysteine, and methionine, respectively, regardless of whether or not the urine values were expressed as $\mu$mol/L or $\mu$mol/10 mmol creatinine. Values for serum total homocysteine and serum methionine were, respectively, 20% and 22% higher, in males than in females ($P<0.05$). Values for serum total cysteine, urine total homocysteine, urine total cysteine, and urine methionine were not significantly different for males and females. Values for serum total homocysteine did not correlate significantly with age, hemoglobin, mean corpuscular volume, white blood cell count, platelet count, serum cobalamin, serum folate, serum methionine, serum total cysteine, or serum methylmalonic acid. The highest correlation coefficients were 0.37 between serum total homocysteine and hemoglobin ($P=0.06$) and $-0.34$ between serum total homocysteine and serum folate ($P=0.06$). The correlation coefficient between serum homocysteine and serum cobalamin was 0.14 ($P=0.44$). The values for serum methionine did not correlate significantly with any of the parameters mentioned above except for hemoglobin where the correlation coefficient was 0.44 ($P<0.05$). The correlation coefficients between serum methionine and serum folate, and serum methionine and serum cobalamin were $-0.09$ ($P=0.64$) and 0.20 ($P=0.29$), respectively. Serum total cysteine was not significantly correlated with any of the parameters mentioned above except for age and serum methylmalonic acid. The correlation coefficients between serum total cysteine and age, and serum total cysteine and serum methylmalonic acid were 0.38 ($P<0.01$) and 0.30 ($P<0.05$), respectively. Values for urine total homocysteine, urine total cysteine, and urine methionine expressed as $\mu$mol/L or $\mu$mol/10 mmol creatinine were not significantly correlated with age, hemoglobin, mean corpuscular volume, white blood cell count, platelet count, serum cobalamin, serum folate, serum methylmalonic acid, serum total homocysteine, serum methionine, or serum total cysteine.

We calculated that the mean urinary clearances of total homocysteine, total cysteine, and methionine from human serum relative to the clearance of creatinine were 0.3%, 0.6%, and 0.1%, respectively. These observations demonstrate that only a small fraction of total homocysteine, total cysteine, and methionine present in serum are excreted in the urine, and that levels and relative changes in the concentrations of these amino acids may thus differ between serum and urine in various pathologic conditions.

We have thus developed and demonstrated techniques which make it possible to detect and quantitate total homocysteine and total cysteine in serum from normal humans and rats and in urine from normal humans. Reduction with a suitable sulfhydryl compound such as 2-mercaptoethanol is essential for measuring total homocysteine and total cysteine in serum because 50% to 70% of these amino acids are covalently bound to serum proteins via disulfide linkage. Our studies and those of others indicate that liberation of this bound homocysteine and cysteine occurs rapidly, but our studies also indicate that the formation of new disulfides following reduction occurs to a significant degree. Detection and quantitation based on mass spectrometry is extremely beneficial in this situation, since one can employ stable isotope forms of homocysteine and cysteine themselves as internal standards. These internal standards equilibrate with endogenous total homocysteine and endogenous total cysteine during the reduction step and remain equilibrated during the partial reformation of new disulfides. It is also possible to omit the initial reduction step and thereby detect and measure the concentrations of free homocystine, free cystine, and free homocysteine-cysteine dimer provided the appropriate internal standards are used. It should be possible to utilize our methodology to measure protein bound homocysteine and cysteine separately, although we have not investigated this. It is also possible to measure other amino acids at the same time utilizing additional appropriate internal standards. We have done this in the case of methionine and have found that the methodology is readily applicable to other amino acids.

We have defined normal ranges for total homocysteine in human and rat serum, and human urine. The values for human serum and urine are similar to those reported recently by Refsum, H., S. Helland, and P. M. Ueland, Clin. Chem. 31(4):624–628 (1985). Our values for human serum are approximately 30% higher than theirs, however, and this may be due in part to the use of a stable isotope form of homocysteine as an internal standard in our procedure with the resultant advantages described above, and in part to the fact that total homocysteine values increase somewhat as samples are allowed to clot at room temperature for several hours as in our procedure.

We have also defined normal ranges for total cysteine in human serum and human urine. Our values with respect to human serum are in good agreement with values reported by Malloy, M. H., D. K. Rassin, and G. E. Gaull, Anal. Biochem. 113:407–415 (1981), who utilized reduction with dithiothreitol followed by the spectrophotometric determination of endogenous total cysteine. The fact that our values are approximately 20% higher may reflect the inclusion of a stable isotope internal standard in our procedure as discussed above. Our values for human urine total cysteine are similar to those reported by Martensson, J., Metabolism 31:487–492 (1982), who utilized a standard amino acid analyzer.

The normal ranges that we determined for methionine in human and rat serum, and human urine are in excellent agreement with values determined by a number of other investigators who used the amino acid analyzer.

Our values for total homocysteine, total cysteine, and methionine in rat serum are similar to the limited data of other investigators.

The availability of a sensitive and specific method for measuring total homocysteine in human serum will have a number of clinical applications that include the following: (i) determinations of the incidence of elevated values for serum total homocysteine in patients with clinically-confirmed cobalamin or folate deficiency, (ii) determination of total homocysteine levels in the serum of patients with low, borderline, or low normal levels of serum cobalamin or serum folate in order to assess the diagnostic sensitivity and specificity of the serum cobalamin and serum folate assays, (iii) determination of total homocysteine levels in the serum of patients with a variety of neuropsychiatric abnormalities and in the elderly in order to better define the incidence of cobalamin and folate deficiencies in these groups, and (iv) determination of total homocysteine levels in heterozygotes for cystathionine synthetase deficiency in an attempt to develop a better diagnostic test for this heterozygous state which is correlated with an increased incidence of peripheral vascular and cerebrovascular disease. The assay of total homocysteine in human serum is a relatively sensitive measure of both cobalamin deficiency and folate deficiency. The ability to measure total homocysteine in the serum of animals such as the rat will also be useful in studies employing nitrous oxide, cobalamin analogues, folate analogues such as methotrexate, and cobalamin- or folate-deficient diets, all of which interfere with various aspects of cobalamin or folate metabolism and utilization.

EXAMPLE IV

Representative Assay for Methylmalonic Acid

According to the method of Marcell, P. D., S. P. Stabler, E. R. Podell, and R. H. Allen, Anal. Biochem. 150:58–66 (1985)

Methylmalonic, succinic, and glutaric acids were purchased from Sigma Chemical company (St. Louis, Mo.), malonic acid was from J. T. Baker Chemical Co. (Phillipsburg, N.J.), and dimethylmalonic, ethylmalonic, and methylsuccinic acids were from Aldrich Chemical Co. (Milwaukee, Wis.). [Methyl-$^2$H$_3$]methylmalonic acid (>99%, via custom synthesis) and [1,4-$^{13}$C$_2$]succinic acid (>99%) were purchased from Merck Sharpe & Dohme Isotopes (Montreal, Canada). [Methyl-$^{14}$C]methylmalonic acid (via custom synthesis) and [1,4-$^{14}$C$_2$]succinic acid were purchased from New England Nuclear Corp. (Boston, Mass.). N-Methyl-N(t-butyldimethylsilyl)trifluoroacetamide was obtained from Pierce Chemical Co. (Rockford, Ill.). All solvents were of high-performance liquid chromatography grade from Burdick & Jackson Laboratories, Inc. (Muskegon, Mich.). Blood samples were obtained from normal healthy donors at the Belle Bonfils Blood Bank, Denver, Colo. at the time of blood donation. Consecutive blood donors were chosen such that samples were obtained from five males and five females in each of the following age groups: 18–26, 27–35, 36–45, 46–55, and 56–65, for a total of 50 samples. The samples were obtained between 9 am and 1 pm, were allowed to clot at room temperature for 1 to 4 h and centrifuged at 1500 g for 30 min, and the serum was removed and stored at $-20°$ C. In addition, other samples were allowed to clot for 0 to 24 h before centrifugation. Spot urine samples were collected from the same 50 individuals within 30 min of when the blood samples were obtained and were also stored at $-20°$ C. Sprague-Dawley rats, 250–350 g, were obtained from SASCO, Inc. (Omaha, Neb.) and blood was obtained by intracardiac puncture under ether anesthesia. Serum was collected and stored as described above for the human blood samples.

A volume of 50 $\mu$l of H$_2$O containing 200 ng of [methyl-$^2$H$_3$]methylmalonic acid and 2000 ng of [1,4-$^{13}$C$_2$]succinic acid was added to 500 $\mu$l of serum or 100 $\mu$l of urine, and an additional 400 $\mu$l of H$_2$O was added to the urine samples. The pH was then raised to about 12 by adding 50 $\mu$l of 2 N NaOH and 5 ml of diethyl ether was then added, followed by vigorous mixing and centrifugation at 1000 g for 3 min, and the upper ether layer was decanted and discarded. The pH was then adjusted to about 1 by adding 50 $\mu$l of 6 N HCl and the samples were extracted twice with 5 ml of diethyl ether as described above. The ether extracts were pooled, taken to dryness by applying a stream of nitrogen in a 40° C. water bath, and then dissolved in 500 $\mu$l of H$_2$O. The entire sample was injected onto a Waters Associates (Milford, Mass.) high-performance liquid chromatography anion-exchange system consisting of a 720 system controller, a 730 data module, two 6000A pumps, a U6K injector, and a Z-module equipped with a Radial Pak SAX cartridge (10 um, 8 mm × 10 cm), and a precolumn (4 × 23 mm) packed with pellicular anion exchanger obtained from Whatman, Inc. (Clifton, N.J.). The mobile phase consisted of 0.05M KH$_2$PO$_4$-H$_3$PO$_4$, pH 2.0, and 2-ml fractions were collected at a flow rate of 2 ml/min. Fractions 3–5 contained greater than 95% of the methylmalonic acid and succinic acid that was injected based on separate experiments performed with [methyl-$^{14}$C]methylmalonic and [1,4-$^{14}$C$_2$]succinic acids, which were used to check the chromatography system on a daily basis. These fractions were pooled, 50 $\mu$l of 6N HCl was added to adjust the pH to approximately 1, and the samples were extracted twice with 5 ml of diethyl ether as described above. These ether extracts were pooled, taken to dryness by applying a stream of nitrogen in a 40° C. water bath, dissolved in 150 $\mu$l of methanol, and transferred to 300-$\mu$l Reactivials (Pierce Chemical Co., Rockford, Ill.), together with a 150 $\mu$l methanol rinse. The samples were then taken to dryness in a Speed Vac vacuum concentrator (Savant Instruments, Inc., Hicksville, N.Y.).

The t-butyldimethylsilyl esters of the dicarboxylic acids were prepared by adding 100 μl of acetonitrile and 10 μl of N-methyl-N-(t-butyldimethylsilyl)trifluoroacetamide to each vial, sealing them with Teflon-lined septum caps, and allowing them to stand at room temperature (22° C.) overnight. H$_2$O, 100 μl, was added to hydrolyze any unreacted derivatizing reagent, followed by the addition of 250 μl hexane, vigorous mixing, and centrifugation at 1000 g for 5 min. The upper hexane layer was decanted, transferred to a separate Reacti-vial, and dried to approximately 5 μl by applying a stream of nitrogen. Care was taken to avoid complete dryness, since this results in a major loss of the derivatives. Approximately 2 μl was injected onto the capillary column of a Hewlett-Packard (Palo Alto, Calif.) 5992B gas chromatograph-mass spectrometer via the falling-needle injector. The gas chromatograph/mass spectrometer was equipped with a 9825B calculator, a 9876A printer, and a molecular jet separator. The injection port was modified to accept the falling-needle injector and an auxiliary make-up carrier gas line was supplied to the jet separator. Sample resolution was achieved on a Durabond DB-5 fused silica capillary column (30 m×0.25 mm i.d., 0.25 um film thickness) from J & W Scientific, Inc. (Rancho Cordova, Calif.). The gas chromatograph/mass spectrophotometer was operated under standard autotune conditions with an injection port temperature of 250° C. and a column head pressure of 22 psi. The capillary column was equilibrated at 160° C. and 6.5 min after sample injection was increased to 188° C. at 8° C./min. Data were collected from 5.8 to 12.5 min using the selected ion monitoring mode. The following [M-57]+ ions were monitored using a 50-ms dwell time for each: malonic acid, m/z 275.2; methylmalonic acid, m/z 289.2; [methyl-$^2$H$_3$]-methylmalonic acid, m/z 292.2; succinic acid, m/z 289.2; [1,4-$^{13}$C$_2$]succinic acid, m/z 291.2; dimethylmalonic acid, m/z 303.2; ethylmalonic acid, m/z 303.2; methylsuccinic acid, m/z 303.2; and glutaric acid, m/z 303.2. Methylmalonic acid was quantitated by dividing the integrated area of the m/z 289.2 peak that eluted at approximately 6.8 min (the exact times were determined daily with standards) by the integrated area of the m/z 292.2 peak that eluted at the same time, and then multiplying by 200 ng, which was the amount of the [methyl-$^2$H$_3$]methylmalonic acid added to each sample. Succinic acid was quantitated in the same manner utilizing the m/z 289.2 and m/z 291.2 peaks that eluted at approximately 9.3 min and multiplying their ratio by 2000 ng, which was the amount of the [1,4-$^{13}$C$_3$]succinic acid added to the samples. The integrated areas for the two internal standard peaks, i.e. the m/z 292.2 and m/z 291.2 peaks eluting at about 6.8 and 9.3 min, respectively, were corrected for the amounts contributed to them by endogenous methylmalonic acid and succinic acid as a result of naturally occurring isotope abundance. These corrections, which were determined for unenriched methylmalonic and succinic acids on a daily basis, were as follows: (i) approximately 1.9% of the area of the m/z 289.2 peak at 6.8 min was present as a m/z 292.2 peak at 6.8 min, and (ii) approximately 10.8% of the area of the m/z 289.2 peak at 9.3 min was present as a m/z 291.2 peak at 9.3 min.

The sensitivity of the assay was measured by determining, e.g., the ratio of methylmalonic acid to [methyl-$^2$H$_3$]methylmalonic acid, at which the standard curve deviates from linearity as described by Zinn, A. B., D. G. Hine, M. J. Mahoney, and K. Tanaka, Pediatr. Res. 16:740–745 (1982).

The urinary clearance of methylmalonic acid and succinic acid from serum, relative to that of creatinine, was determined with the following equation as illustrated for methylmalonic acid: methylmalonic acid/creatinine clearance ratio=100×[urine methylmalonic acid (ng/ml)/urine creatinine (ng/ml)]/[serum methylmalonic acid (ng/ml)/serum creatinine (ng/ml)].

The extensive nature of the partial sample purification utilized in this procedure was necessary because of the complex mixture of organic compounds found in serum, and because of the relatively low concentrations of methylmalonic acid that are present. Procedures using extractions with various organic solvents followed by a further purification with small anion-exchange or reverse-phase columns were unsatisfactory. High-performance liquid chromatography using an anion-exchange resin proved to be very beneficial, since the low pK$_a$ values of the dicarboxylic acids under study resulted in their being retarded at pH 2, while most other compounds were not retarded. Analysis of urine samples may not require the same degree of partial purification as is necessary for serum. Experiments in which known amounts of [methyl-$^{14}$C]methylmalonic acid and [1,4-$^{14}$C]succinic acids were added to serum and urine samples showed that 10 to 20% of both dicarboxylic acids were recovered in the final hexane solution at the end of the extensive partial purification and derivatization procedures.

Initial attempts to produce the t-butyldimethylsilyl derivatives of dicarboxylic acids using a mixture of t-butyldimethylchlorosilane/N,N-dimethylformamide/imidazole (Applied Science Laboratories, Inc., State College, Pa.) as described by de Jong, A. P. J. M., J. Elema, and B. J. T. van de Berg, Biomed. Mass Spectrom. 7:359–364 (1980) were unsatisfactory for quantitative work due to marked variations in the degree of derivatization and due to the relative instability of the derivatives. Questions concerning the unexpected ease with which some t-butyldimethylsilyl derivatives, such as esters of certain organic acids, are hydrolyzed have been raised in the past. We found that the pH of the reaction mixture as described by de Jong et al. was approximately 1, and that this resulted in the hydrolysis of the newly-formed t-butyldimethylsilyl derivatives of the dicarboxylic acids due to an inability of the imidazole to completely scavenge the HCl produced by the reaction involving the chlorosilane. This problem was only partially corrected by the addition of other acid scavengers such as pyridine. We found, however, that the t-butyldimethylsilyl derivatives prepared with N-methyl-N-(t-butyldimethylsilyl)trifluoroacetamide were obtained in high yield, in a reproducible manner, and were stable for more than a week after their extraction into hexane as described above. This procedure was therefore adopted as our standard method.

The structure and m/z value of the t-butyldimethylsilyl derivative of methylmalonic acid is shown below together with the fragmentation positions and the m/z values of the major fragments of interest which are at [M-57]+ and [M-15]+:

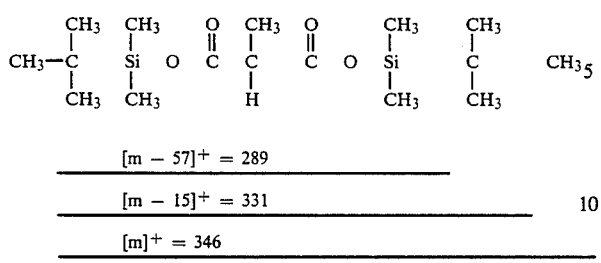

| | |
|---|---|
| $[m-57]^+ = 289$ | |
| $[m-15]^+ = 331$ | |
| $[m]^+ = 346$ | |

Figure 4:
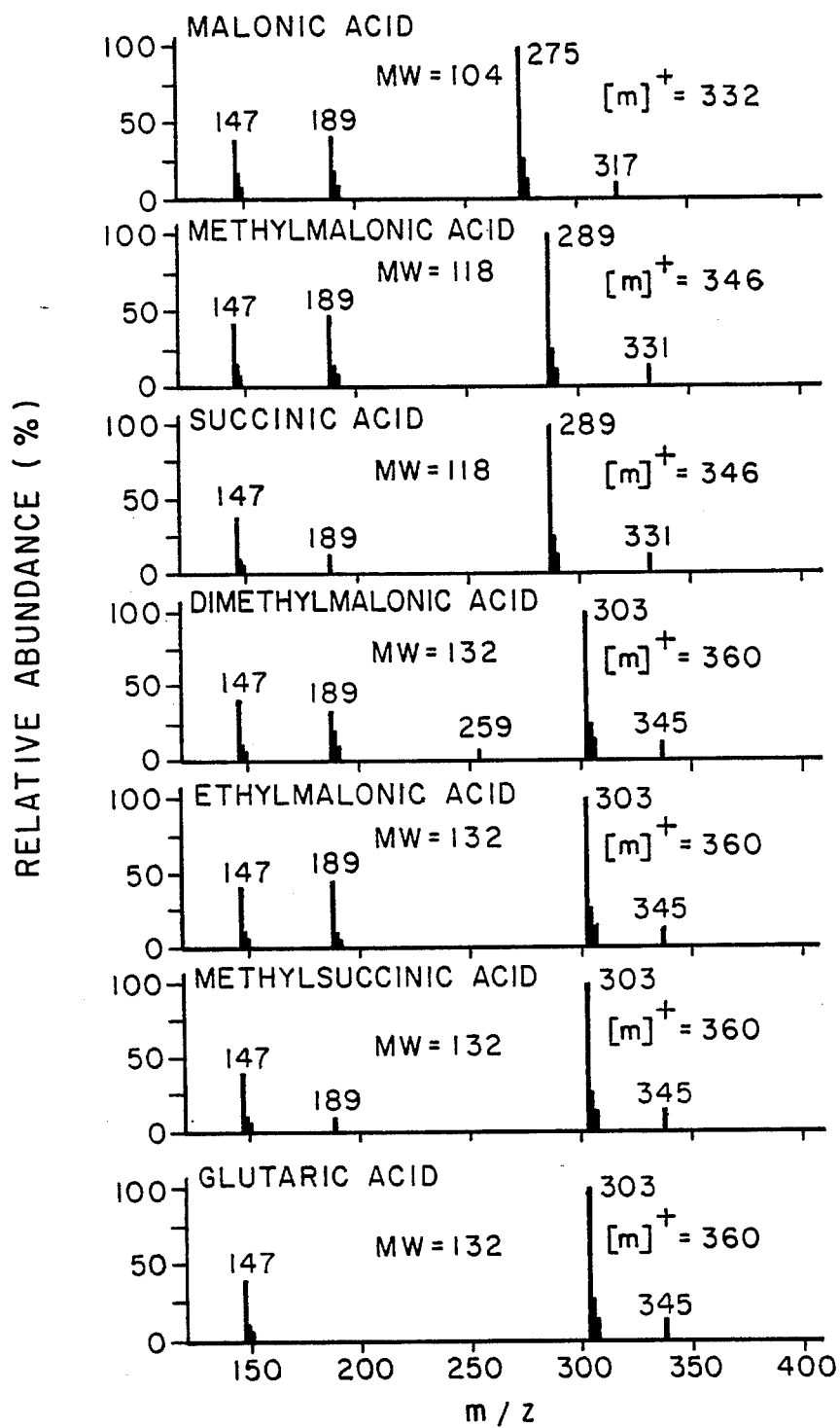
FIG. 4 illustrates the molecular weights of dicarboxylic acids together with the mass spectra of their t-butyldimethylsilyl derivatives.

The molecular weights of malonic, methylmalonic, succinic, dimethylmalonic, ethylmalonic, methylsuccinic, and glutaric acids are shown in FIG. 4 together with the mass spectra of their t-butyldimethylsilyl derivatives. The molecular weight of a particular derivative is equal to the molecular weight of the dicarboxylic acid plus 228 due to the addition of two t-butyldimethylsilyl groups. Peaks representing the entire derivative, i.e., $[M]^+$, were not observed for any of the dicarboxylic acids. Rather, the major peak in each case was $[M-57]^+$, which represented 35-45% of the sum of all the peaks in the m/z range of 100 to 400. Smaller peaks representing $[M-15]^+$ were also observed for each dicarboxylic acid derivative, although the amounts were only 3-6% of the amounts present for the $[M-57]^+$ peaks. Peaks with a value of m/z 147 were observed with all of the dicarboxylic acid derivatives and peaks with a value of m/z 189 were observed with all except for the glutaric acid derivative. Both of these peaks appear to result from fragmentation and rearrangement of portions of the t-butyldimethylsilyl groups themselves, and do not involve portions of the dicarboxylic acids themselves because abundant m/z 147 and m/z 189 peaks were also observed with [methyl-$^2$H$_3$]methylmalonic acid and [1,4-$^{13}$C$_2$]succinic acid.

Figure 5:
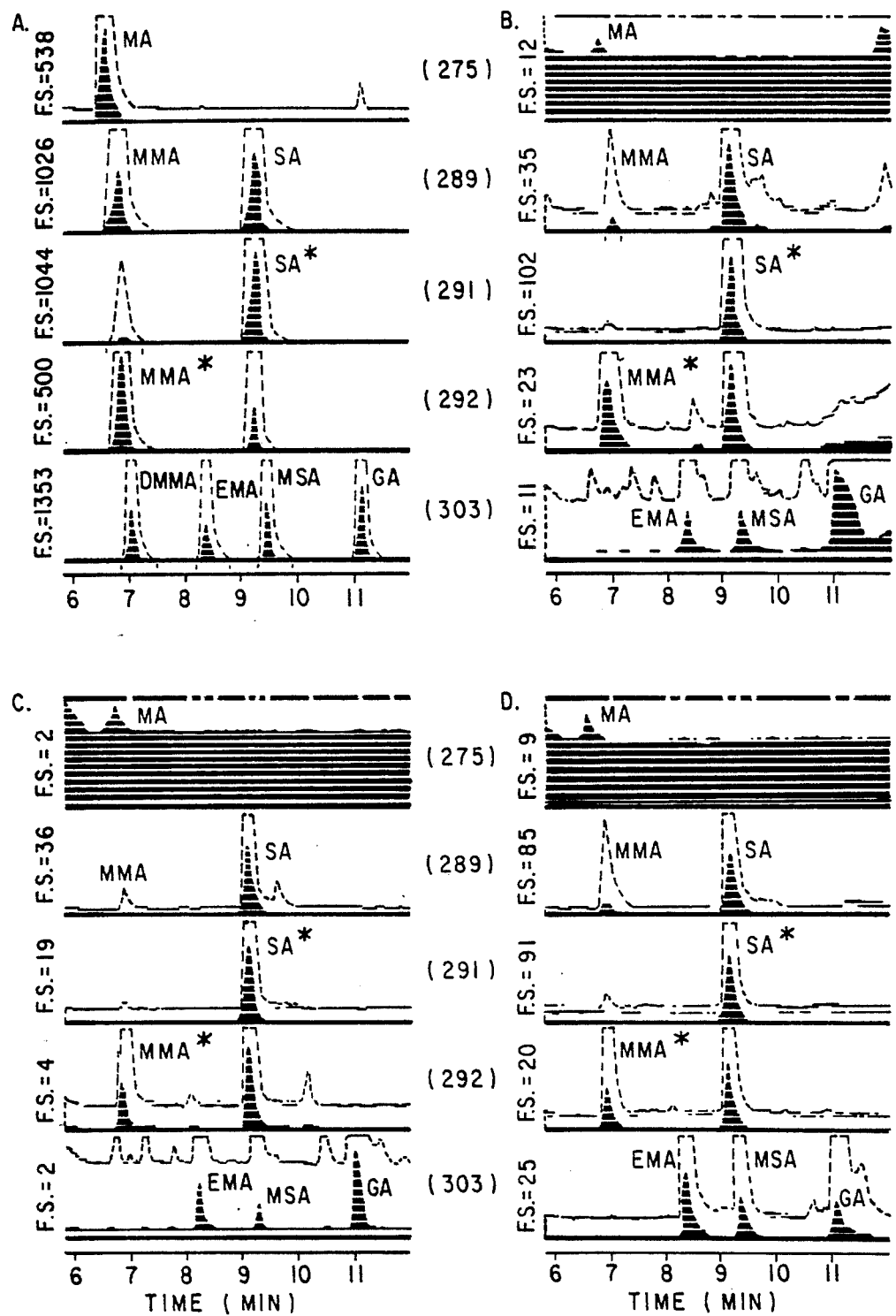
FIGS. 5A, B, C and D illustrate the chromatograms of the t-butyldimethylsilyl derivatives of dicarboxylic acids.

FIG. 5 shows chromatograms of the t-butyldimethylsilyl derivatives of dicarboxylic acids obtained from (A) a mixture containing 1 μg of each acid; (B) 500 μl of pooled normal human serum; (C) 500 μl of normal rat serum; and (D) 100 μl of normal human urine. The acids studied were malonic acid (MA), methylmalonic acid (MMA), succinic acid (SA), [1,4-$^{13}$C$_2$]succinic acid (SA*), [methyl-$^2$H$_3$]methylmalonic acid (MMA*), dimethylmalonic acid (DMMA), ethylmalonic acid (EMA), methylsuccinic acid (MSA), and glutaric acid (GA). Numbers in parentheses are the values for m/z that were scanned by selected ion monitoring. Values for "F.S." are the relative values for the full scale of the heavy-dashed tracing; the light-dashed tracing is a 10X attenuation. Values determined for MMA were 56, 92, and 3400 ng/ml for B, C, and D, respectively. Values determined for SA were 1110, 9200, and 19,000 ng/ml for B, C, and D, respectively.

FIG. 5A demonstrates that the capillary column gives a complete separation for all of the derivatives that have the same molecular weight, i.e., methylmalonic acid and succinic acid are completely separated from each other, and dimethylmalonic acid, ethylmalonic acid, methylsuccinic acid, and glutaric acid are completely separated from one another. Methylmalonic acid is not completely separated from dimethylmalonic acid nor is succinic acid completely separated from methylsuccinic acid, but this is not a problem, since, as shown in FIG. 4, these unresolved dicarboxylic acid derivatives have different molecular weights and mass spectra and thus there is no interference when selected ion monitoring is used.

Studies with samples of human serum and urine and rat serum, in which [methyl$^2$H$_3$]methylmalonic and [1,4$^{13}$C$_2$]succinic acids were not added demonstrated that substances that might interfere with their use as internal standards for quantitation were not present. The sensitivity of the assays were 5 ng for methylmalonic acid and 150 ng for succinic acid under the standard conditions that used 200 ng of [methyl$^2$H$_3$]methylmalonic acid and 2000 ng of [1,4$^{13}$C$_2$]succinic acid, although the sensitivities could be improved in each case by decreasing the amounts of the internal standards added. Assays performed under standard conditions showed that the assay for methylmalonic acid was linear from 5 to 5000 ng, and that the assay for succinic acid was linear from 150 to 150,000 ng in aqueous samples and in serum samples to which known amounts of the respective acids were added.

A chromatogram obtained with 500 μl of pooled normal human serum is shown in FIG. 5B. Succinic acid is present in the largest amount and malonic, methylmalonic, ethyl malonic, methylsuccinic, and glutaric acids are present in smaller, but readily detected, amounts. Dimethylmalonic acid could not be detected with certainty. Chromatograms obtained with 500 μl of normal rat serum and 100 μl of normal human urine are shown in FIGS. 5C and D, respectively, and are similar to the chromatogram obtained with pooled normal human serum (FIG. 5B).

Studies performed with a single sample of pooled normal human serum that was repeatedly frozen and thawed and assayed on seventeen different occasions over a 10-month period gave values for the coefficient of variation of 26 and 19% for the assay of methylmalonic acid and succinic acid, respectively. No significant change or trend in the values for these two dicarboxylic acids was observed over the 10-month period. Values for serum methylmalonic acid obtained with blood samples that were drawn and immediately centrifuged at 4° C. were the same as those obtained with portions of the same blood samples that were incubated at room temperature for 1 or 24 h prior to centrifugation. Values for serum succinic acid increased over this time period, however, with an approximate increase of 10% being noted after the 1 h room temperature incubation and an approximate 90% increase being noted after the 24 hour incubation. Studies performed with rat serum gave similar results. Values for urine methylmalonic and succinic acids were unchanged when urine samples were incubated at room temperature for 0 to 24 h.

The values for the actual mean (ng/ml) and range obtained for methylmalonic and succinic acids in serum samples from 50 normal human subjects and 95 normal rats, calculated as the mean ±2 S.D. after log transformation to correct for skewness towards higher values were: human serum methylmalonic acid, 41 (19-76); human serum succinic acid, 1270 (580-2420); rat serum methylmalonic acid, 128 (42-295); and rat serum succinic acid 11900 (5420-22800). The values for the actual mean (ng/ml or ng/mg creatinine) and range obtained for urine samples from the same 50 normal human subjects, calculated as defined above, were: human urine methylmalonic acid, 1840 (270-7190); human urine methylmalonic acid/mg urine creatinine, 2010 (810-3830); human urine succinic acid, 25400 (4620-85600); and human urine succinic acid/mg urine creatinine, 28200 (8360-75100). The normal ranges for methylmalonic and succinic acids in urine are tighter when expressed as ng/mg creatinine than when expressed as ng/ml.

Values for methylmalonic and succinic acids were both significantly higher in rat serum than in human serum. Neither human serum methylmalonic acid nor human serum methylmalonic acid per milligram serum creatinine correlated significantly with urine methylmalonic acid or urine methylmalonic acid per milligram urine creatinine. The values for serum and urine methylmalonic acid were not significantly different for males and females and did not correlate significantly with age, hemoglobin, mean corpuscular volume, white blood count, platelet count, serum cobalamin, serum folate, serum creatinine, serum succinic acid, or urine succinic acid. The highest correlation coefficient was $-0.25$ between serum methylmalonic acid and serum cobalamin ($P=0.08$). Serum and urine succinic acid levels were not significantly correlated with any of the parameters mentioned above for methylmalonic acid.

We calculated that the mean urinary clearance of methylmalonic acid from human serum relative to the clearance of creatinine was 28%, and the mean urinary clearance of succinic acid from human serum relative to the clearance of creatinine was 13%. This observation supports the concept that most of the methylmalonic acid in serum is metabolized via unknown pathways, as has been observed in experiments in which [methyl-$^{14}$C]methylmalonic acid was administered to rats via intracardiac injections.

Our studies support the suggestions of de Jong et al. since we have shown that the t-butyldimethylsilyl derivatives of a number of dicarboxylic acids have excellent gas chromatographic and mass spectrometric properties. Initially, we encountered problems of a serious nature due to variable degrees of derivatization and hydrolytic instability, but these problems were solved by substituting N-methyl-N-(t-butyldimethylsilyl) trifluoroacetamide as the derivatizing reagent in place of the t-butyldimethylchlorosilane/N,N-dimethylformamide/imidazole mixture utilized by de Jong et al. This improvement is also applicable to preparing and quantitating t-butyldimethylsilyl derivatives of other compounds of biologic interest that contain carboxylic or other groups that are particularly susceptible to hydrolysis, and to the derivatization and quantitation of other amino acids.

We have developed techniques which make it possible to detect and to quantitate methylmalonic acid in serum from normal humans and rats. We have also defined the normal range for methylmalonic acid in human urine and our values are in general agreement with values obtained with other gas chromatography-mass spectrometry techniques. Our method is also suitable to quantitate malonic, dimethylmalonic, ethylmalonic, methylsuccinic, glutaric, and other dicarboxylic acids in serum and urine, although an appropriate stable isotope internal standard for each dicarboxylic acid should be utilized to ensure optimal quantitative accuracy.

The availability of a sensitive and specific method for measuring methylmalonic acid in human serum has a number of clinical applications that include the following: (i) determination of the incidence of elevated values for serum methylmalonic acid in patients with clinically confirmed cobalamin deficiency, (ii) determination of methylmalonic acid levels in the serum of patients with low, borderline, and low normal levels of serum cobalamin in order to assess the diagnostic sensitivity and specificity of the serum cobalamin assay, and (iii) determination of methylmalonic acid levels in the serum of patients with a variety of neuropsychiatric abnormalities, and in the elderly in order to better define the incidence of cobalamin deficiency in these groups. The assay of methylmalonic acid in human serum is a relatively sensitive measure of cobalamin deficiency, and the ability to measure methylmalonic acid in the serum of animals such as the rat will also be useful in studies employing nitrous oxide, cobalamin analogs, or cobalamin-deficient diets, all of which interfere with various aspects of cobalamin metabolism and utilization.

EXAMPLE V

Assay of Methylmalonic Acid in the Serum of Patients with Cobalamin Deficiency

Serum samples from 50 normal blood donors, 25 males and 25 females, ranging in age from 18 to 65 years were obtained as described in Example II. Patient samples were selected from an extensive serum collection that has been assembled over the past 15 years. The diagnosis of cobalamin (Cbl) deficiency was based on low serum Cbl levels, megaloblastic bone marrow morphology, appropriate hematologic or neurologic abnormalities, and a significant response to treatment with parenteral Cbl. The diagnosis of pernicious anemia was based on an abnormal Schilling test [see, e.g., Beck, W. S., in *Hematology* (W. J. Williams, E. Beutler, A. J. Ersler, and M. A. Lichtman, eds.)(McGraw-Hill Book Co., New York, 1983), pp. 444–445]that corrected with exogenous intrinsic factor and/or the presence of anti-intrinsic factorblocking antibodies in the serum. The diagnosis of folate deficiency was based on low serum folate values, normal or elevated serum Cbl values, megaloblastic bone marrow morphology, appropriate hematologic abnormalities, and a history of alcoholism and poor diet. The samples in the Cbl-deficient infrequently treated group were from patients with pernicious anemia who were previously diagnosed as Cbl deficient as described above, but who received only intermittent treatment with parenteral Cbl at intervals of 6–9 months due to poor compliance or as part of other studies of Cbl requirements. They had low, borderline, or normal levels for serum Cbl, lacked hematologic and neurologic abnormalities, and were asymptomatic at the time the samples were collected. Serum Cbl levels were assayed using the *Lactobacillus leichmannii* method [see, e.g., Matthews, D. M., Clin. Science 22:101(1962)]or a number of radiodilution assays utilizing purified intrinsic factor or gastric juice with more than 95% of Cbl binding activity due to intrinsic factor [Kolhouse, J. F., H. Kondo, N. C. Allen, E. Podell, and R. H. Allen, N. Eng. J. Med. 299:785–792(1978)]. Serum folate was assayed with the *Lactobacillus casei* method [Goulian, M. and W. S. Beck, Am. J. Clin. Path. 46:390(1966)]or the milk binder radiodilution assay [Rothenberg, S. P., et al., N. Eng. J. Med. 286:1335 (1972)]. All of the patients' samples were coded in a manner such that the categories to which they belonged and the number of patients in each category were not known by the personnel involved in performing the methylmalonic acid and succinic acid assays.

A number of factors were examined individually for possible relationships with serum methylmalonic acid and succinic acid. For factors that were discrete, such as sex, race and diagnosis, the Wilcoxon two-sample test

[Steel, R. G. D. and J. H. Torrie, *Principles and Procedures of Statistics* (McGraw-Hill Book Co., Inc., New York, 1960]was used to determine the significance of the relation. For assessing possible relationships with neurologic severity, groups 0, 1, and 2 (as defined in Table 1) were combined and compared with combined groups 3 and 4. Factors that were continuous, such as age or mean corpuscular volume (MCV), were examined using Spearman correlative coefficients [Steel, supra]. Results are given in Table I:

TABLE I

| Patient | Age | Serum Cbl pg/ml | Serum Folate ng/ml | Hct % | MCV fl | Neuro-abnormalities[a] | Diagnosis[b] | Succinic Acid ng/ml | Serum MMA ng/ml |
|---|---|---|---|---|---|---|---|---|---|
| Normals | | 200–1000 | 3–25 | M 40–52 F 35–47 | 80–100 | 0 | 0 | 580–2,240 | 19–76 |
| 1 | 81 | 115 | 19.3 | 26 | 135 | 0 | 0 | 780 | 22,300 |
| 2 | 61 | 68 | 25.5 | 30 | 108 | 3 | PA | 2,090 | 22,200 |
| 3 | 17 | 78 | 50.0* | 39 | 109 | 4 | IR | 4,030 | 21,900 |
| 4 | 56 | 23 | 15.0 | 20 | 106 | 2 | PA | 1,890 | 9,500 |
| 5 | 68 | 145 | 50.0 | 38 | 104 | 3 | PA | 430 | 9,090 |
| 6 | 86 | 10 | 3.8 | 11 | 112 | 2 | PA | 1,670 | 8,300 |
| 7 | 64 | 122 | 50.0 | 18 | 130 | 3 | PA | 7,600 | 7,410 |
| 8 | 65 | 36 | 5.7 | 17 | 132 | 3 | PA | 1,850 | 6,200 |
| 9 | 72 | 17 | 9.7 | 14 | 111 | 3 | PA | 1,840 | 5,800 |
| 10 | 69 | 85 | 48.0 | 28 | 111 | 3 | PA | 1,730 | 5,790 |
| 11 | 51 | 125 | 14.3 | 38 | 106 | 3 | PA | 1,950 | 5,640 |
| 12 | 65 | 78 | 13.0 | 16 | 122 | 2 | PA | 4,070 | 5,560 |
| 13 | 63 | 60 | 26.0 | 31 | 117 | 0 | PA | 255 | 5,370 |
| 14 | 62 | 75 | 8.8 | 38 | 110 | 3 | PA | 2,770 | 4,800 |
| 15 | 72 | 110 | 3.4 | 45 | 101 | 3 | PA | 2,200 | 4,800 |
| 16 | 61 | 10 | 15.0 | 25 | 120 | 3 | PA | 1,235 | 4,580 |
| 17 | 64 | 48 | 28.0 | 19 | 118 | 0 | PA | 2,571 | 4,180 |
| 18 | 76 | 26 | 3.6 | 30 | 115 | 1 | PA | 2,420 | 3,900 |
| 19 | 56 | 132 | 4.7 | 22 | 98 | 0 | PA | 1,310 | 3,400 |
| 20 | 67 | 125 | 29.0 | 35 | 109 | 0 | PA | 1,780 | 3,350 |
| 21 | 72 | 58 | >29.0 | 29 | 121 | 0 | TS | 740 | 2,950 |
| 22 | 54 | 50 | 25.0 | 33 | 117 | 3 | PA | 1,940 | 2,790 |
| 23 | 78 | 70 | 8.6 | 11 | 83 | 3 | PA | 1,610 | 2,740 |
| 24 | 17 | 10 | 28.5 | 12 | 105 | 0 | PA | 2,650 | 2,660 |
| 25 | 82 | 74 | 14.0 | 24 | 132 | | PA | 2,190 | 2,500 |
| 26 | 47 | 150 | 11.0 | 31 | 109 | 3 | PA | 908 | 2,080 |
| 27 | 53 | 115 | 20.0 | 21 | 107 | 1 | TS | 1,270 | 1,990 |
| 28 | 92 | 73 | 4.1 | 41 | 114 | | PA | 10,900 | 1,870 |
| 29 | 72 | 66 | 50.0* | 27 | 106 | 3 | MJD | 1,190 | 1,770 |
| 30 | 54 | 62 | >29.0 | 19 | 118 | 3 | PA | 2,260 | 1,700 |
| 31 | 88 | 130 | 7.0 | 34 | 115 | 2 | PA | 2,910 | 1,530 |
| 32 | 65 | 140 | 9.2 | 15 | 115 | 2 | PA | 1,030 | 1,530 |
| 33 | 69 | 44 | 19.0 | 20 | 113 | 2 | PA | 1,310 | 1,380 |
| 34 | 52 | 10 | 28.0 | 18 | 108 | 1 | PA | 1,020 | 1,320 |
| 35 | 83 | 150 | 4.3 | 35 | 113 | 0 | PA | 1,070 | 1,160 |
| 36 | 68 | 81 | 3.8 | 20 | 135 | 0 | TS | 1,560 | 1,160 |
| 37 | 22 | 44 | 3.3 | 16 | 120 | 1 | PA | 8,420 | 1,120 |
| 38 | 88 | 45 | 28.0 | 22 | 137 | 3 | PA | 460 | 1,100 |
| 39 | 61 | 150 | 5.7 | 18 | 99 | 0 | PA | 2,500 | 1,040 |
| 40 | 66 | 150 | 14.7 | 36 | 117 | 0 | PA | 1,460 | 751 |
| 41 | 56 | 64 | 6.9 | 18 | 126 | 3 | PA | 1,010 | 637 |
| 42 | 70 | 136 | | 33 | 118 | 0 | PA | 1,430 | 536 |
| 43 | 82 | 135 | 17.0* | 35 | 105 | 0 | PA | 2,090 | 526 |
| 44 | 66 | 120 | 2.4 | 15 | 119 | | PA | 1,520 | 518 |
| 45 | 42 | 20 | 4.8 | 25 | 126 | 0 | PA | 2,980 | 465 |
| 46 | 80 | 50 | 6.3 | 38 | 115 | 2 | PA | 3,150 | 453 |
| 47 | 70 | 120 | 3.8 | 38 | 103 | 1 | PA | 1,340 | 399 |
| 48 | 84 | 68 | 15.8 | 26 | 118 | 4 | PA | 1,240 | 386 |
| 49 | 72 | 95 | 1.9 | 27 | 115 | 0 | PA | 2,200 | 352 |
| 50 | 80 | 129 | 3.8 | 35 | 110 | 0 | PA | 1,160 | 340 |
| 51 | 73 | 60 | 5.5 | 44 | 97 | 3 | PA | 1,761 | 335 |
| 52 | 35 | 50 | 11.0 | 13 | 110 | 0 | PA | 2,350 | 300 |
| 53 | 69 | 98 | 5.2 | 36 | 119 | 4 | PA | 1,880 | 273 |
| 54 | 59 | 90 | 1.2 | 14 | 100 | 0 | TS | 2,640 | 272 |
| 55 | 26 | 140 | 2.1 | 29 | 117 | 0 | TS | 1,120 | 272 |
| 56 | 70 | 130 | | 22 | 126 | 1 | PA | 2,200 | 270 |
| 57 | 85 | 43 | 2.8 | 15 | 125 | 1 | TS | 1,360 | 231 |
| 58 | 83 | 125 | 10.5 | 43 | 103 | | PA | 1,720 | 194 |
| 59 | 59 | 67 | 6.8 | 31 | 116 | 0 | PA | 2,510 | 170 |
| 60 | 72 | 45 | 41.0 | 42 | 84 | 4 | PA | 1,290 | 169 |
| 61 | 70 | 130 | 12.4 | 14 | 115 | 2 | PA,IR | 1,460 | 154 |
| 62 | 55 | 65 | 9.1 | 29 | 118 | 0 | IR,PG | 2,470 | 152 |
| 63 | 80 | 78 | | 33 | 101 | 3 | PA | 27,900 | 149 |
| 64 | 81 | 16 | 1.2 | 34 | 82 | 0 | PA | 9,720 | 149 |
| 65 | 52 | 93 | 9.9 | 45 | 109 | 0 | PA | 1,610 | 139 |
| 66 | 41 | 110 | 5.6 | 29 | 132 | 0 | PG | 3,350 | 137 |
| 67 | 76 | 74 | 14.5 | 39 | 102 | 0 | PA | 1,640 | 116 |
| 68 | 29 | 76 | 5.7 | 30 | 108 | 0 | PA | 1,770 | 111 |
| 69 | 51 | 35 | 8.5 | 22 | 118 | 0 | TS | 1,490 | 78 |
| 70 | 65 | 96 | 3.6 | 16 | 114 | 2 | TS | 1,420 | 73 |

TABLE I-continued

| Patient | Age | Serum Cbl pg/ml | Serum Folate ng/ml | Hct % | MCV fl | Neuro-abnor mali-ties[a] | Diag-nosis[b] | Succinic Acid ng/ml | Serum MMA ng/ml |
|---|---|---|---|---|---|---|---|---|---|
| 71 | 55 | 106 | 2.1 | 18 | 108 | 0 | TS | 1,590 | 61 |
| 72 | 70 | 62 | 2.3 | 27 | 121 | 0 | PA | 2,340 | 59 |
| 73 | 50 | 87 | 5.9 | 38 | 105 | 0 | TS | 1,840 | 55 |

[a]4 = severe advanced combined systems disease; 3 = combined systems disease or severe dysfunction responsive to Cbl treatment (Nos. 2 and 63); 2 = no neurological symptoms but impairment of position and/or vibration sense on exam; 1 = paresthesias with negative neurological exam

[b]IR = ileal resection; MJD = multiple jejunal diverticula; PA = pernicious anemia; PG = postgastrectomy; TS =0 tropical sprue

*receiving folic acid

Figure 6:
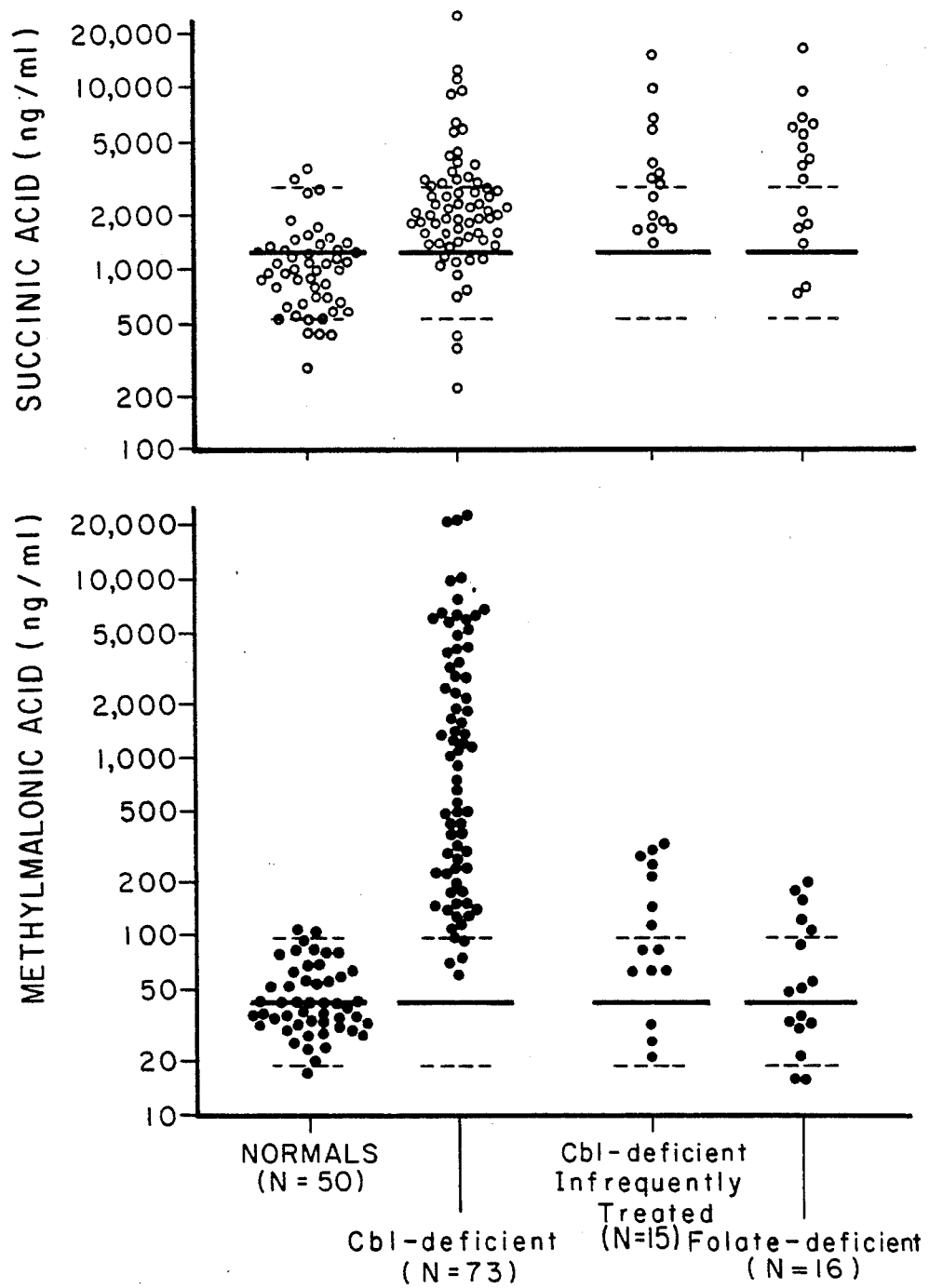
FIG. 6 is a graphic representation of serum methylmalonic acid and succinic acid values in cobalamin deficient, folate deficient, and normal subjects.

The values obtained for serum methylmalonic acid and succinic acid for the normal subject and patients in the various categories are shown in FIG. 6, wherein levels of serum methylmalonic acid (bottom) and serum succinic acid (top) are given for patients with clinically confirmed Cbl deficiency, folate deficiency, and Cbl-deficient infrequently treated patients who had no hematologic or neurologic abnormalities. The normal range for methylmalonic acid is 19-76 ng/ml, and 580-2420 ng/ml for succinic acid. The ranges were calculated as mean ±2 S.D. after log transformation to correct for skewness towards higher values. In the Cbl-deficient group, 69 of the 73 patients had values for methylmalonic acid that were above the normal range of 19-76 ng/ml. The highest value was 22,300 ng/ml and the median value was 1,100 ng/ml. Five of the 16 folate-deficient patients had mild elevations of serum methylmalonic acid with the highest value being 140 ng/ml. Seven of 15 samples from the Cbl deficient infrequently-treated patients who lacked hematologic and neurologic abnormalities had elevated values that ranged as high as 175 ng/ml. Of these seven samples, serum *L. leichmannii* Cbl concentrations were low (88-165 pg/ml) in six and normal (275 pg/ml) in one. All seven samples gave low Cbl values (85-155 pg/ml) with radiodilution assay using purified intrinsic factor. Of the eight samples with normal levels of methylmalonic acid; serum *L. leichmannii* Cbl was low in four.

Elevated values for serum succinic acid were observed in 19 of the 73 Cbl-deficient patients, 10 of the 16 folate-deficient patients, and 8 of the 15 Cbl-deficient infrequently treated patients. The reason for these elevations is unknown, but could be related to variations in the time that blood is allowed to stand before the serum is separated, since we have found that values for succinic acid may double when blood is allowed to stand for 24 h at room temperature before centrifugation. Values for serum methylmalonic acid do not change over this time period.

Clinical data concerning the 73 patients with Cbl deficiency are presented in Table I where they are arranged in decreasing order with respect to their serum methylmalonic acid levels. There was a significant correlation between serum methylmalonic acid and serum folate ($r=0.45$, $P<0.001$). The correlation was present in samples measured by the *L. casei* serum folate method ($r=0.46$; $P<0.01$) as well as the radioassay technique ($r=0.66$; $P<0.001$). Patients with more severe neurologic abnormalities (groups 3 and 4) had higher serum methylmalonic acid levels (mean ±SD, 5077±6073, median 3685 ng/ml) than those with milder abnormalities (groups 1 and 2, mean 2083±2866, median 879 ng/ml) or no evidence of neurological involvement (group 0, mean 1154±1468, median 409 ng/ml) ($P<0.01$ for groups 3 and 4 vs. 0-2).

Serum folate levels correlated with serum methylmalonic acid regardless of neurologic status (r for methylmalonic acid vs. folate in patients without neurologic disorders, 0.58; n=27; $P<0.01$). Although serum folate concentrations were higher in patients with more severe neurological abnormalities (mean serum folate in groups 3 and 4, 20.9±16.9 vs 10.1±8.7 ng/ml in groups 0-2, $P<0.005$), the association of higher serum methylmalonic acid levels with advanced neurological involvement appears to be independent of folate status. In patients with serum folate levels below 15 ng/ml, mean serum and methylmalonic acid in groups 3 and 4 was 3189±2317 ng/ml vs 1030±1795 ng/ml in groups 0-2 ($P<0.005$); serum folates did not differ significantly between the two subgroups (7.5±3.3 vs. 6.0±3.8 ng/ml, respectively, $P<0.25$).

There was a negative correlation between the platelet count and serum methylmalonic acid levels ($r=-0.30$; $P<0.05$). However, the correlation was no longer significant if patients with more severe neurologic abnormalities (groups 3 and 4) were omitted from the analysis ($r=-0.26$; $P>0.05$) or if patients with elevated serum folates were omitted ($r=-0.23$; $P>0.05$). Patients with pernicious anemia had higher values for serum methylmalonic acid (mean, 2968±4387 ng/ml) than those with tropical sprue (714±1007, $P<0.004$ using Mann-Whitney test [Steel, supra]; when corrected for the generally lower serum folate values and less severe neurologic involvement in the patients with tropical sprue, however, the difference was no longer significant. Patients with glossitis had higher serum methylmalonic acid values than patients without tongue signs or symptoms; however, 13 of the 18 patients with glossitis with serum levels of methylmalonic acid above the median for the entire group of 73 patients had severe neurologic involvement, elevated serum folate values, or both.

Serum methylmalonic acid was not correlated with serum Cbl ($r=-0.09$ for all patients; $r=0.12$ for microbiologic assay; and $-0.09$ for radioassays, $P>0.4$ in each instance). Serum methylmalonic acid was not significantly correlated with MCV ($r=0.07$, $P>0.05$), white blood cells ($r=-0.08$; $P>0.3$), or hematocrit ($r=-0.12$; $P>0.4$). All of the 12 patients with normal hematocrits had elevated serum methylmalonic acid levels (range 116-4800 ng/ml). There was no correlation between serum methylmalonic acid and age, sex, race, duration of symptoms, extent of weight loss, or serum levels of iron, lactate dehydrogenase (LDH), bilirubin, or albumin.

Four patients with untreated Cbl deficiency (Nos 70-73, Table I) had serum methylmalonic acid levels within the normal range. Three had tropical sprue. One of the four had impaired proprioception and vibration sense without neurological symptoms. There were no clinical or laboratory features that differentiated these patients from those with elevated serum methylmalonic acid concentrations.

Values for serum succinic acid did not correlate with any of the parameters studied, including serum methylmalonic acid, and significant differences were not observed between any of the various subgroups.

Figure 7:
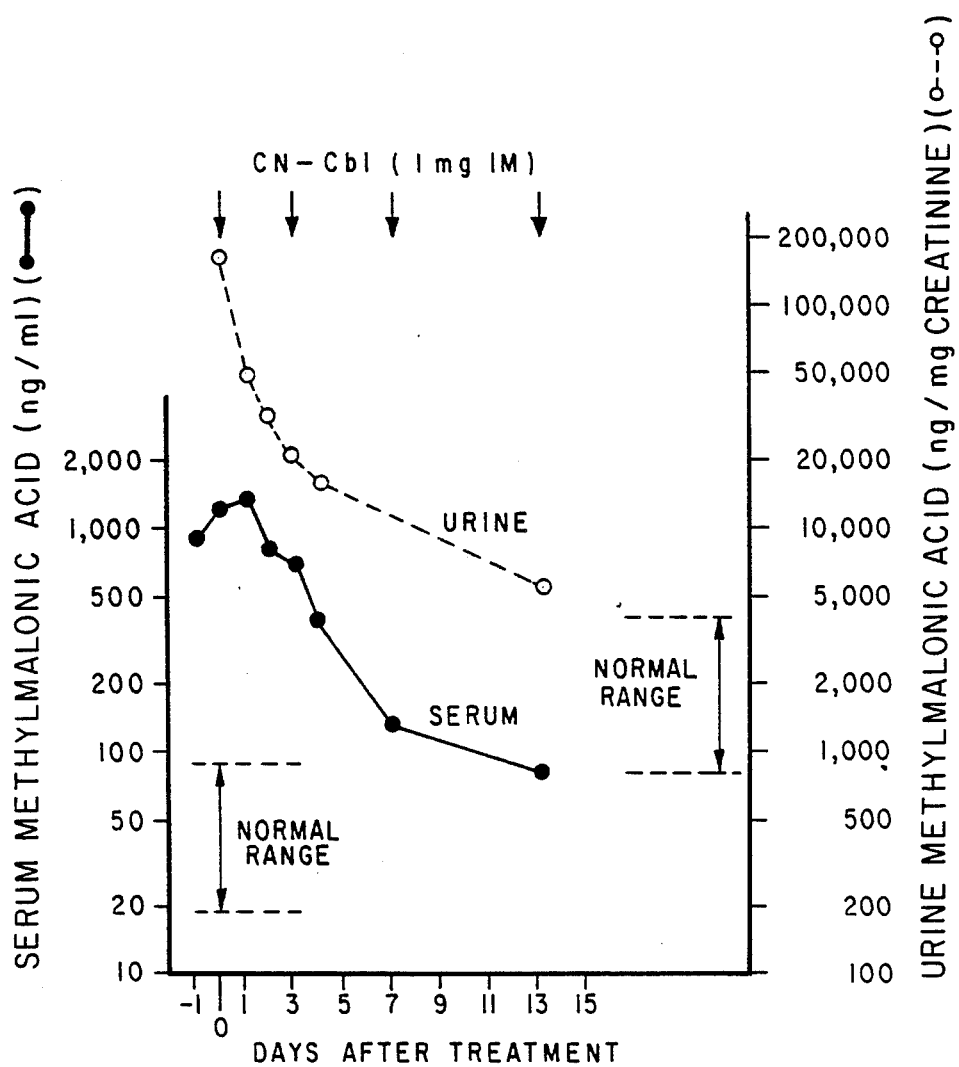
FIG. 7 is a graphic representation of sequential serum and urine metylmalonic acid levels in a subject with classic pernicious anemia.

FIG. 7 shows sequential levels of serum (—·—) and urine (--o--) methylmalonic acid in a patient with classic pernicious anemia, beginning at the time of diagnosis and continuing over the first 13 days after treatment with parenteral Cbl. The patient was a 32-year old white male with pancytopenia, megaloblastic bone marrow findings, a serum Cbl value of 43 pg/ml, serum anti-intrinsic factor-blocking anti-bodies, and an abnormal Schilling test that corrected with exogenous intrinsic factor. Both values were markedly elevated before treatment, both decreased at similar rates after treatment, and both were just above the upper limit of normal on day 13. This suggests that measurements of serum and urine methylmalonic acid would correlate well with one another as diagnostic tests for Cbl deficiency, but a large number of additional patients must be studied before this can be concluded with certainty.

Table II contains data regarding a 95-year old white female in whom an elevated serum methylmalonic acid level preceded a low serum Cbl level:

TABLE II

|  | Normal | 9/30/82 | 8/23/83* | 9/13/83 | 8/20/84 |
| --- | --- | --- | --- | --- | --- |
| MCV (fl) | 80–100 | 105 | 104 | 102 | 94 |
| Hgb (g/dl) | 13.5–16.7 | 12.4 | 12.1 | 12.4 | 12.4 |
| Serum Cbl (pg/ml)[a] | 207–1098 | 237,230[b] | 47 |  |  |
| Serum folate (ng/ml) | 2.4–17.5 | 14.0,13.1[b] | 10.0 |  |  |
| Anti-intrinsic factor-blocking antibodies | absent | present[b] | present |  |  |
| Serum MMA (ng/ml) | 19–76 | 269[b] | 338 | 32 |  |
| Urine MMA (ng/mg creatinine) | 810–3830 | no sample | 11,000 | 1,480 |  |

*The patient started receiving monthly intramuscular injections of 1 mg CN-Cbl on 8/23/83 after the serum and urine were collected.
[b]radiodilution assay using purified intrinsic factor (>95%) as the Cbl-binding protein
[a]These values were obtained on the serum sample taken 9/30/82, tested in early August 1983

In September 1982 she was asymptomatic but noted to have an MCV of 105 which led to the performance of serum Cbl and folate assays which gave normal values. This serum was stored for almost 1 year while the serum methylmalonic acid assay was being developed, and gave an elevated value of 269 ng/ml when it was finally assayed in August 1983. Repeat assays in August 1983 for serum Cbl and serum folate on the August 1982 sample were again normal, and antiintrinsic factor-blocking antibodies were assayed and found to be present. In August 1983 the patient was recalled to clinic where her MCV was essentially unchanged. The serum methylmalonic acid level was still elevated at 338 ng/ml and methylmalonic acid was elevated in the urine, but the serum Cbl level was now markedly decreased. Three weeks after receiving an injection of Cbl, serum and urine methylmalonic acid levels had fallen to within the normal range and, when rechecked a year later, the MCV was 94. No neuropsychiatric symptoms were noted at any time. A high unsaturated Cbl-binding capacity is an unlikely explanation for this patient since her white blood cell count has never (September 1982 - mid-1986) been elevated and her unsaturated Cbl-binding capacity was normal (2.1 ng/ml) just before treatment with Cbl (Aug. 23, 1983). Unfortunately, Cbl-binding capacity was not measured on the September 1982 sera.

Our studies demonstrate that the assay of methylmalonic acid in serum provides useful information in patients with Cbl deficiency. The fact that the serum methylmalonic acid level was elevated in 69 of 73 patients with clinically confirmed Cbl deficiency and in 7 of the 15 samples from the Cbl-deficient infrequently treated group who lacked hematologic or neurologic abnormalities, suggests that its sensitivity may be similar to that of the serum Cbl level, although studies of patients with borderline and low normal values for serum Cbl must be performed before a complete comparison of the two assays can be made. The fact that we have observed a patient in whom a moderate elevation of serum methylmalonic acid preceded the development of a low serum Cbl level suggests that the serum methylmalonic acid level will correctly detect Cbl deficiency in at least some patients in whom the serum Cbl level does not. Thus, it is likely that the serum methylmalonic acid assay and the serum Cbl assay will complement each other, and that using both assays will make it possible to define the true incidence of Cbl deficiency in various patient populations in a more thorough manner than would be possible with either test alone. The specificity of the serum methylmalonic acid assay for Cbl deficiency may prove to be greater than that of the serum Cbl level, which is frequently low in patients with no clinical evidence of deficiency or of an underlying condition affecting Cbl balance. The test may also prove to be useful in the evaluation of patients with megaloblastic anemia in whom serum levels of both Cbl and folate are subnormal.

The serum methylmalonic acid level has one advantage that is not shared by the serum Cbl level in that one can treat a patient suspected of being Cbl-deficient with Cbl and observe the effect on the serum methylmalonic acid level. If such treatment results in a decrease in the serum methylmalonic acid level from the elevated to the normal range, this is strong presumptive evidence that the patient was Cbl-deficient, as was the case with the patient described in detail in this report. This advantage is not shared by the serum Cbl level, since serum levels of Cbl are essentially always elevated or at least normal after parenteral injection of Cbl, regardless of whether a patient is Cbl-deficient or not.

Mild, but significant elevations in serum methylmalonic acid were observed in 5 of 16 folate-deficient patients who had normal serum Cbl levels. Two of these five patients had hepatomegaly and/or abnormal liver function tests and three had no evidence of liver disease. Studies involving measurements of urinary methylmalonic acid have also shown mild elevations in a few patients with folate deficiency, but it is not known if this is due to mild coincidental Cbl deficiency or to some other unknown cause. Recent studies have shown that the amount of Cbl in various tissues is insufficient to saturate both Cbl-dependent enzymes. It is possible that in folate deficiency an attempt is made to increase levels of methionine synthetase activity by increasing the amount of Cbl bound to methionine synthetase with the result that the amount of Cbl bound to L-methylmalonyl-CoA mutase is decreased, and that this in turn results in increased formation of methylmalonic acid (see FIG. 1).

Levels of serum methylmalonic acid were not correlated with levels of serum Cbl in the Cbl-deficient patient group. A correlation between Cbl levels and levels of urinary methylmalonic acid was observed previously in some studies but not in others. The failure to find correlations between serum methylmalonic acid levels and any of the hematologic parameters, except for a weak inverse correlation with platelet count, is in agreement with studies employing levels of urinary methylmalonic acid.

Previous workers, studying small numbers of patients with neurologic abnormalities, have found no correlation with urine levels of methylmalonic acid or have suggested a possible relationship. The positive correlation between serum methylmalonic acid levels and the presence of neurologic abnormalities in our large series of patients is of interest, since the biochemical mechanisms responsible for the neurologic abnormalities in Cbl deficiency are still unknown. The positive correlation between serum folate levels and serum methylmalonic acid levels has also not been noted in studies of urinary methylmalonic acid levels. This correlation could be due to the fact that patients on diets with relatively high folate contents might have fewer hematologic abnormalities, possibly resulting in a delay in the diagnosis of Cbl deficiency. The fact that values for serum folate were not positively correlated with any hematologic parameter makes this unlikely, however. It is also possible that some unknown metabolic or regulatory relationship exists between L-methylmalonyl-CoA mutase and methionine synthetase in addition to the fact that they both require Cbl for activity.

Inspection of Table I reveals that many of the cobalamin deficient patients were not anemic, or only moderately anemic, were not macrocytic or only moderately macrocytic, and did not have markedly decreased serum Cbl levels below 100 pg/ml. These observations are in disagreement with the current beliefs and teachings of experts in the medical field (see above) and will be discussed in more detail at the end of the next example

EXAMPLE VI

Use of the Assay of Total Homocysteine Alone or of the Combined Homocysteine-Methylmalonic Acid Assays in the Diagnosis and distinction of Cobalamin and Folate Deficiency Serum samples from 78 patients with confirmed Cbl deficiency and 19 patients with confirmed folate deficiency were tested for serum Cbl and serum folate as described in Example V, for serum methylmalonic acid as described in Example IV, and serum methionine, serum cysteine and serum homocysteine as described in Example III. The results are given in Table III:

TABLE III

| Patient | Age | Serum Cbl pg/ml | Serum Folate ng/ml | Hct % | MCV fl | Neuro Abnormalities[a] | Diagnosis[b] | Serum MMA ng/ml | Serum Met umol/L | Serum Total Cys umol/L | Serum Total Hcys umol/L |
|---|---|---|---|---|---|---|---|---|---|---|---|
| Normal | | 200–1000 | | M 40–52 F 35–47 | 80–100 | 0 | 0 | 19–76 | 14–44 | 174–378 | 7–22 |
| Cobalamin-deficient | | | | | | | | | | | |
| 1 | 61 | 68 | 26.0 | 30 | 108 | 3 | PA | 22,200 | 43 | 216 | 476 |
| 2 | 64 | 122 | 50.0 | 18 | 130 | 3 | PA | 7,410 | 24 | 321 | 399 |
| 3 | 68 | 81 | 3.8 | 20 | 135 | 0 | TS | 1,160 | 30 | 190 | 299 |
| 4 | 71 | 145 | 10.0 | 40 | 119 | 3 | PA | 1,711 | 60 | 489 | 289 |
| 5 | 76 | 26 | 3.6 | 30 | 115 | 1 | PA | 3,900 | 18 | 316 | 258 |
| 6 | 17 | 10 | 28.5 | 12 | 105 | 0 | PA | 2,660 | 28 | 178 | 251 |
| 7 | 61 | 10 | 15.0 | 25 | 120 | 3 | PA | 4,580 | 18 | 262 | 228 |
| 8 | 88 | 150 | 10.0 | 19 | 120 | 4 | PA | 7,449 | 41 | 318 | 223 |
| 9 | 52 | 10 | 28.0 | 18 | 108 | 1 | PA | 1,320 | 35 | 228 | 205 |
| 10 | 65 | 78 | 13.0 | 16 | 122 | 2 | PA | 5,560 | 41 | 571 | 196 |
| 11 | 67 | 125 | 29.0 | 35 | 109 | 0 | PA | 3,350 | 116 | 127 | 196 |
| 12 | 78 | 70 | 8.6 | 11 | 83 | 3 | PA | 2,740 | 27 | 190 | 187 |
| 13 | 83 | 50 | 10.7 | 39 | 115 | 4 | PA | 2,220 | 34 | 291 | 187 |
| 14 | 56 | 64 | 8.7 | 18 | 126 | 3 | PA | 637 | 35 | 206 | 184 |
| 15 | 54 | 50 | 25.0 | 33 | 117 | 3 | PA | 2,790 | 21 | 229 | 183 |
| 16 | 56 | 25 | 15.0 | 20 | 106 | 2 | PA | 9,500 | 24 | 255 | 182 |
| 17 | 62 | 75 | 8.8 | 38 | 110 | 3 | PA | 4,800 | 67 | 210 | 174 |
| 18 | 42 | 20 | 4.8 | 25 | 126 | 0 | PA | 465 | 102 | 220 | 173 |
| 19 | 72 | 110 | 3.4 | 45 | 101 | 3 | PA | 4,800 | 29 | 330 | 170 |
| 20 | 69 | 85 | 48.0 | 28 | 111 | 3 | PA | 5,790 | 28 | 151 | 163 |
| 21 | 65 | 50 | 5.5 | 45 | 123 | | PA | 7,470 | 41 | 348 | 160 |
| 22 | 69 | 44 | 19.0 | 20 | 113 | 2 | PA | 1,380 | 32 | 300 | 157 |
| 23 | 53 | 115 | 20.0 | 21 | 107 | 1 | TS | 1,990 | 38 | 236 | 153 |
| 24 | 56 | 132 | 4.7 | 22 | 98 | 0 | PA | 3,400 | 27 | 286 | 151 |
| 25 | 81 | 115 | 19.3 | 26 | 135 | | PA | 22,300 | 33 | 235 | 150 |
| 26 | 68 | 145 | 50.0 | 38 | 104 | 3 | PA | 9,090 | 18 | 208 | 149 |
| 27 | 86 | 10 | 38.0 | 11 | 112 | 0 | PA | 8,300 | 38 | 280 | 146 |
| 28 | 54 | 62 | >29.0 | 19 | 118 | 3 | PA | 1,700 | 34 | 200 | 140 |
| 29 | 65 | 140 | 9.2 | 15 | 115 | 2 | PA | 1,530 | 26 | 250 | 130 |
| 30 | 88 | 45 | 28.0 | 22 | 137 | 3 | PA | 1,100 | 28 | 126 | 128 |
| 31 | 54 | 45 | 3.5 | 21 | 111 | 4 | PA | 1,770 | 24 | 241 | 128 |
| 32 | 22 | 44 | 3.3 | 16 | 120 | 1 | PA | 1,120 | 42 | 264 | 126 |
| 33 | 65 | 36 | 5.7 | 17 | 132 | 3 | PA | 6,200 | 129 | 209 | 120 |
| 34 | 72 | 58 | >29.0 | 29 | 121 | 0 | TS | 2,950 | 18 | 159 | 118 |

TABLE III-continued

| Patient | Age | Serum Cbl pg/ml | Serum Folate ng/ml | Hct % | MCV fl | Neuro Abnormalities[a] | Diagnosis[b] | Serum MMA ng/ml | Serum Met umol/L | Serum Total Cys umol/L | Serum Total Hcys umol/L |
|---|---|---|---|---|---|---|---|---|---|---|---|
| 35 | 64 | 48 | 28.0 | 19 | 118 | 0 | PA | 4,180 | 120 | 160 | 117 |
| 36 | 28 | 120 | 32.0 | 31 | 99 | 0 | PA | 2,735 | 32 | 158 | 117 |
| 37 | 66 | 120 | 2.4 | 15 | 119 |  | PA | 518 | 30 | 351 | 114 |
| 38 | 47 | 150 | 11.0 | 31 | 109 | 3 | PA | 2,080 | 66 | 295 | 113 |
| 39 | 61 | 150 | 5.7 | 18 | 99 | 0 | PA | 1,040 | 38 | 208 | 113 |
| 40 | 51 | 125 | 14.3 | 38 | 106 | 3 | PA | 5,640 | 139 | 67 | 111 |
| 41 | 66 | 150 | 50.0 | 36 | 117 | 0 | PA | 751 | 18 | 329 | 109 |
| 42 | 92 | 73 | 4.1 | 41 | 114 |  | PA | 1,870 | 51 | 509 | 106 |
| 43 | 84 | 68 | 15.8 | 26 | 118 | 4 | PA | 386 | 19 | 348 | 99 |
| 44 | 80 | 50 | 6.3 | 38 | 115 | 2 | PA | 453 | 76 | 505 | 97 |
| 45 | 40 | 10 | 7.4 | 22 | 109 | 3 | PA | 280 | 37 | 304 | 97 |
| 46 | 88 | 130 | 7.0 | 34 | 115 | 2 | PA | 1,530 | 64 | 360 | 95 |
| 47 | 47 | 135 | 11.7 | 14 | 109 | 2 | PA | 7,605 | 11 | 168 | 95 |
| 48 | 84 | 130 |  | 39 | 99 | 4 | PA | 2,620 | 23 | 305 | 93 |
| 49 | 70 | 62 | 3.1 | 27 | 121 | 0 | PA | 59 | 37 | 230 | 92 |
| 50 | 85 | 43 | 2.8 | 15 | 125 | 1 | TS | 231 | 45 | 218 | 89 |
| 51 | 17 | 78 | 50.0* | 39 | 109 | 4 | IR | 21,900 | 37 | 207 | 88 |
| 52 | 41 | 110 | 7.3 | 29 | 132 | 0 | PG | 137 | 36 | 106 | 86 |
| 53 | 83 | 150 | 4.3 | 35 | 113 | 0 | PA | 1,160 | 64 | 366 | 83 |
| 54 | 72 | 95 | 32.0 | 27 | 115 | 0 | PA | 352 | 34 | 279 | 80 |
| 55 | 73 | 60 | 5.5 | 44 | 97 | 3 | PA | 335 | 20 | 279 | 78 |
| 56 | 70 | 120 | 3.8 | 38 | 103 | 1 | PA | 399 | 28 | 426 | 76 |
| 57 | 35 | 50 | 11.0 | 13 | 110 | 0 | PA | 300 | 12 | 157 | 75 |
| 58 | 81 | 16 | 12.0 | 34 | 82 | 0 | PA | 149 | 14 | 398 | 73 |
| 59 | 62 | 10 | 5.2 | 20 | 112 | 0 | PA | 132 | 57 | 264 | 73 |
| 60 | 59 | 90 | 1.2 | 14 | 100 | 0 | TS | 272 | 64 | 272 | 73 |
| 61 | 65 | 96 | 7.5 | 16 | 114 | 2 | TS | 73 | 17 | 215 | 69 |
| 62 | 70 | 130 | 12.4 | 14 | 115 | 2 | PA,IR | 154 | 34 | 206 | 68 |
| 63 | 20 | 10 | 12.0 | 35 | 129 | 0 | PA | 1,656 | 48 | 210 | 64 |
| 64 | 69 | 98 | 5.2 | 36 | 119 | 4 | PA | 273 | 30 | 393 | 63 |
| 65 | 50 | 67 | 6.8 | 31 | 116 | 0 | PA | 170 | 32 | 261 | 60 |
| 66 | 70 | 130 | 8.5 | 22 | 126 | 1 | PA | 270 | 21 | 187 | 58 |
| 67 | 51 | 35 | 8.5 | 22 | 118 | 0 | TS | 78 | 45 | 198 | 55 |
| 68 | 72 | 45 | 41.0 | 42 | 84 | 4 | PA | 169 | 35 | 390 | 47 |
| 69 | 71 | 170 | 7.8 | 23 | 114 | 2 | PA | 333 | 16 | 232 | 45 |
| 70 | 70 | 136 | 3.0 | 33 | 118 | 0 | PA | 536 | 106 | 440 | 42 |
| 71 | 82 | 135 | 17.0* | 35 | 105 | 0 | PA | 526 | 59 | 304 | 38 |
| 72 | 52 | 93 | 9.9 | 45 | 109 | 0 | PA | 139 | 24 | 273 | 36 |
| 73 | 73 | 150 | 2.9 | 28 | 105 | 0 | PG | 17 | 28 | 211 | 34 |
| 74 | 80 | 129 | 3.8 | 35 | 110 | 0 | PA | 340 | 84 | 360 | 32 |
| 75 | 29 | 76 | 5.7 | 30 | 108 | 0 | PA | 111 | 33 | 248 | 30 |
| 76 | 76 | 74 | 11.5 | 39 | 102 | 0 | PA | 116 | 23 | 224 | 28 |
| 77 | 83 | 125 | 10.5 | 43 | 103 |  | PA | 194 | 19 | 276 | 27 |
| 78 | 50 | 87 | 5.9 | 38 | 105 | 0 | TS | 55 | 26 | 163 | 11 |
| Folate-deficient | | | | | | | | | | | |
| 79 | 42 | 790 | 0.5 |  | 11 | 0 | ALC,P | 47 | 27 | 210 | 185 |
| 80 | 41 | 420 | 0.5 |  | 12 | PN | ALC,P | 15 | 39 | 193 | 135 |
| 81 | 59 | 520 | 0.6 | 32 | 114 | 0 | ALC,P | 79 | 30 | 238 | 133 |
| 82 | 52 | 3150 | 0.5 | 8 | 100 | 0 | ALC,P | 37 | 81 | 252 | 132 |
| 83 | 78 | 375 | 2.0 | 18 | 110 | 0 | ALC,P | 92 | 21 | 273 | 95 |
| 84 | 64 | 1070 | 1.2 | 25 | 142 | 0 | ALC,P | 53 | 29 | 326 | 93 |
| 85 | 31 | 425 | 2.3 | 33 | 114 | PN | ALC,P | 36 | 27 | 91 | 83 |
| 86 | 47 | 1160 | 1.1 | 15 | 108 | PN | ALC,P | 47 | 61 | 193 | 80 |
| 88 | 38 | 780 | 1.5 | 13 |  | 0 | ALC,P | 130 | 19 | 395 | 67 |
| 89 | 77 | 340 | 0.8 | 28 | 104 | 0 | ALC,P | 195 | 39 | 352 | 56 |
| 90 | 53 | 750 | 0.9 | 18 | 114 | PN | ALC,P | 152 | 33 | 281 | 50 |
| 91 | 36 | 1340 | 1.3 | 8 | 116 | 0 | ALC,P | 49 | 32 | 196 | 49 |
| 92 | 87 | 420 | 0.8 | 15 | 83 | 0 | PD | 27 | 20 | 164 | 49 |
| 93 | 37 | 170 | 0.1 | 13 | 123 | 0 | ALC,P | 108 | 19 | 137 | 43 |
| 94 | 53 | 370 | 1.0 | 27 | 112 |  | ALC,P | 73 | 33 | 179 | 37 |
| 95 | 47 | 200 | 0.1 | 12 | 122 | 0 | ALC,P | 15 | 56 | 248 | 36 |
| 96 | 46 | 1110 | 0.5 | 33 | 114 | 0 | TS | 22 | 18 | 144 | 26 |
| 97 | 26 | 1950 | 1.9 | 27 | 123 | 0 | ALC,P | 32 | 23 | 152 | 17 |

[a] 4 = severe advanced combined systems disease; 3 = combined systems disease or severe cerebral dysfunction responsive to Cbl treatment, no neurological symptoms but impairment of position and/or vibration sense on exam; 1 = paresthesia with negative neurological exam; PN = peripheral neuropathy associated with alcoholism
[b] IR = ileal resection; MJD = multiple jejunal diverticulitis; PA = pernicious anemia; PG = postgastrectomy; TS = tropical sprue; ALC,P = alcoholism with poor diet; PD = poor diet
*receiving folic acid Some, but not all, of the patients in Table III are shown in Table I also. Serum homocysteine was elevated (normal 7-22 μmol/L) in 77/78 (99%) of the patients with cobalamin deficiency and 18/19 (95%) of the patients with folate deficiency. In the cobalamin-deficient patients, serum methylmalonic acid was increased in 74/78 (95%)(normal 19-76 pg/ml). In 3 of the cobalamin-deficient patients with a normal serum methylmalonic acid level, the serum total homocysteine was elevated (range 34-93 μmol/L) and in only one patient were both the serum methylmalonic acid and serum total homocysteine within their respective normal ranges. In the folate-deficient patients, 5/19 (26%) had mild elevations of serum methylmalonic acid (range 92-195 ng/ml). Serum methionine levels were not useful in diagnosing cobalamin or folate deficiency as only 2/78 (3%) of the cobalamin-deficient patients and none of the folate-deficient patients had low levels (normal range 14-44 μmol/L). In addition, serum total cysteine levels were not useful diagnostically, since only 6/78 (8%) of the cobalamin-deficient patients had mild elevations and only 1/19 (5%) of the folate-deficient patients had an elevated value (normal range 174-378 μmol/L).

As can be seen in Table III, only 32/78 (41%) of the patients had a moderately severe anemia (Hct<25%), 28/78 (36%) had a moderate anemia (25-34% females, 25-39% males), and 18/78 (23%) were not anemic at all. Only 45/78 (58%) had a marked elevation in MCV (>110 fl), 24/78 (31%) had a mildly elevated MCV (101-110 fl), and 9/78 (11%) had a normal MCV (80-100 fl). The serum level of cobalamin was markedly decreased (<100 pg/ml) in only 48/78 (62%) patients and was only modestly (100-200 pg/ml) decreased in 30/78 (38%). Thus, the spectrum of findings in cobalamin deficiency is much broader than previously believed and one cannot rely on the findings of moderately severe anemia, a markedly depressed serum cobalamin level and a markedly increased MCV in order to make the diagnosis. However, by measuring the serum total homocysteine alone or in combination with the serum methylmalonic acid in these patients one can establish the diagnosis of cobalamin deficiency even when it is associated with mild or absent abnormalities in Hct, MCV, and serum cobalamin levels. The measurement of other amino acids such as serum methionine or total cysteine was not shown to be useful diagnostically in cobalamin deficiency, despite earlier teachings that serum methionine was low in patients with cobalamin deficiency [see, e.g., Parry, T. E., Brit. J. Haemat. 16:221(1969)].

EXAMPLE VII

Confirmation of the Diagnosis of Cobalamin Deficiency in Patients with Neurologic Abnormalities and Mild or No Hematologic Using the Assay for Homocysteine or the Cobmined Homocysteine-Methylmalonic Acid Assay Neurologic abnormalities are often thought to be a late manifestation of Cbl deficiency and to occur rarely if at all in the absence of anemia or macrocytosis. To test this concept, we reviewed 143 consecutive patients with neurologic abnormalities due to CBL deficiency. We found that in 42 of these patients (29%), the hematocrit (35/42), or MCV (26/42), or both tests (19/42) were normal. Other hematologic parameters, when measured, were also frequently normal: WBC (42/42), platelets (40/42), LDH (25/38) and bilirubin (30/31). In these 42 patients, the neurologic abnormalities included distal sensory defects (35), paresthesias (29), ataxia (21), memory loss (12), personality changes (4), spastic paraparesis (3), hallucinations (2), fecal incontinence (2), obtundation (2), optic atrophy (1), and suicide (1). Serum Cbl levels (normal 200-1000 pg/ml) varied considerably as follows : <50 pg/ml (6); 50-100 pg/ml (19), 100-150 pg/ml (12); 150-200 pg/ml (3); and 200-250 pg/ml (2). The diagnosis of Cbl deficiency was confirmed in all 42 patients by demonstrating one or more of the following: a clear elevation of serum methylmalonic acid (MMA) of >150 ng/ml as measured by the procedure of Example IV, normal 18-76 ng/ml, (36/38); a clear elevation of serum homocysteine (Hcys) of >30 μmol/L as measured by the procedure of Example III, normal=7-22 μmol/L, (37/38); a marked decrease in serum MMA (28/28) and serum Hcys (27/28) after Cbl treatment; a decrease of 5 fl or more in the MCV after Cbl treatment (29/35) including most patients (13/16) in whom the MCV was not elevated prior to Cbl treatment; and improvement in neurologic abnormalities after Cbl treatment (39/39).

As can be seen above, only 108 (76%) out of 143 consecutive patients with neurologic abnormalities due to cobalamin deficiency had anemia (Hct<35 female, <40 male) and 35/143 (24%) were not anemic at all. In 26 (18%) of these 143 patients, the MCV was normal and in 19/143 (13%), both the hematocrit and the MCV were normal. In the subset of 42 patients who had either a normal hematocrit, normal MCV or both, only 5/42 (12%) had a marked elevation in MCV (>10 fl), 11/42 (26%) had a mildly elevated MCV (101-110 fl), and 26/42 (62%) had a normal MCV (80-100 fl). The serum level of cobalamin was markedly decreased (<100 pg/ml) in only 24/42 (57%) patients and was only modestly decreased (100-200 pg/ml) in 16-42 (38%). In fact, 2/42 (5%) patients actually had a normal serum cobalamin level. Thus, in these patients with neurologic abnormalities resulting from cobalamin deficiency, the spectrum of hematologic abnormalities is much broader than previously realized and one cannot rely on the findings of moderately severe anemia, a markedly increased MCV, and a markedly depressed serum cobalamin level in order to make the diagnosis of cobalamin deficiency. However, by measuring the serum total homocysteine alone or in combination with the serum methylmalonic acid in these patients one can establish the diagnosis of cobalamin deficiency in patients with only mild abnormalities in Hct, MCV, and serum cobalamin levels. In addition, by monitoring the fall in elevated values of serum total homocysteine and serum methylmalonic acid, one can confirm the diagnosis of cobalamin deficiency, and one can monitor the response to treatment with cobalamin.

We conclude the following: (1) neurologic abnormalities due to Cbl deficiency occur commonly in the absence of anemia or an elevated MCV; (2) measurements of serum MMA and serum Hcys, and changes after Cbl treatment in serum MMA, serum Hcys, and the MCV are useful in evaluating patients for Cbl deficiency; (3) all patients with unexplained neurologic abnormalities should be evaluated for Cbl deficiency even if anemia, macrocytosis, or other hematologic abnormalities are not present; and (4) the clinical spectrum of cobalamin deficiency is wider than previously presumed as can be seen by the lack of anemia or elevated MCV in patients with neurologic disease secondary to cobalamin deficiency which has been confirmed by a fall in elevated serum total homocysteine or serum methylmalonic acid levels after treatment.

While we have illustrated and described the preferred embodiments of this invention, it is to be understood that this invention is capable of variation and modification, and we therefore do not wish to be limited to the precise terms set forth, but desire to avail ourselves of such changes and alternations which may be made for adapting the invention to various usages and conditions. Accordingly, such changes and alterations are properly intended to be within the full range of equivalents, and therefore within the purview, of the following claims.

We claim:

1. A method of assaying for the amount of one or more sulfhydryl amino acid species present in a given sample, said method comprising:
   (a) combining said sample with an internal reference standard comprising a known amount of each sulfhydryl amino acid species to be assayed, labelled with a suitable marker;
   (b) adding sufficient reducing agent to insure randomization of the labelled and unlabelled sulfhydryl amino acids present;
   (c) measuring the relative amounts of labelled and unlabelled sulfhydryl amino acid present for each species with a mass spectrometer;
   (d) calculating the ratio of labelled to unlabelled sulfhydryl amino acid present for each species; and
   (e) deriving the amount of unlabelled sulfhydryl amino acid present for each species in said given sample.

2. The method of claim 1, wherein said labelled and unlabelled amino acids are derivatized after step (b) and before step (c).

3. The method of claim 2, wherein said derivatized amino acids are silyl derivatives.

4. The method of claim 3, wherein said silyl derivatives are obtained by exposing said amino acids to N-methyl-N-(t-butyldimethylsilyl)trifluoro- acetamide.

5. The method of claim 1 or 2 wherein said given sample comprises a body tissue from a warm-blooded animal.

6. The method of claim 5, comprising the additional step of partially purifying the sulfhydryl-containing amino acid after step (b) and before step (c).

7. The method of claim 5 wherein said sulfhydryl-containing amino acid is homocysteine.

8. The method of claim 7 wherein said internal reference standard comprises a known amount of deuterated homocysteine.

9. The method of claim 8, comprising the additional step of partially purifying the homocysteine after step (b) and before step (c).

10. The method of claim 1, comprising the additional step of assaying concurrently for one or more nonsulfhydryl amino acids by providing a non-sulfhydryl amino acid internal reference standard in step (a), measuring the amount of labelled and unlabelled non-sulfhydryl amino acids present with a mass spectrophotometer in step (c), calculating the ratio of standard to each unlabelled non-sulfhydryl amino acids present in step (d), and deriving therefrom the amount of unlabelled non-sulfhydryl amino acid present in said given sample in step (e).

11. The method of claim 10, wherein said nonsulfhydryl amino acid is methionine.

12. The method of claim 10, wherein said non-sulfhydryl amino acid internal reference standard in step (a) is norleucine.

13. A method for detecting a deficiency of cobalamin or folate in warm-blooded animals comprising the steps of:
   assaying a body fluid for an elevated level of total homocysteine; and
   correlating an elevated level of total homocysteine in said body fluid with a deficiency of cobalamin or folate.

14. A method for detecting a deficiency of cobalamin or folate in warm-blooded animals comprising the steps of:
   assaying a body fluid for an elevated level of total homocysteine according to the method of claim 7; and
   correlating an elevated level of total homocysteine in said body fluid with a deficiency of cobalamin or folate.

15. The method of claim 13 wherein said assay for the presence of an elevated level of total homocysteine comprises subjecting a sample of body fluid to chromatography.

16. The method of claim 15 wherein said assay for the presence of an elevated level of total homocysteine comprises subjecting a sample of body fluid to high performance liquid chromatography with an electrochemical detector set to respond to thiol groups, and comparing the results with a standard curve to determine the amount of total homocysteine present in the original sample.

17. The method of claim 13 wherein the assay for the presence of an elevated level of total homocysteine comprises converting homocysteine present in the sample to labelled S-adenosylhomocysteine by exposure to radioactively labelled S-adenosine and S-adenosylhomocysteine hydrolase, and quantifying said labelled S-adenosylhomocysteine.

18. A method for detecting a deficiency of cobalamin, folate, or both in warm-blooded animals and distinguishing therebetween comprising assaying body fluids for the presence of elevated levels of total homocysteine and methylmalonic acid, wherein normal levels of total homocysteine indicate no cobalamin or folic acid deficiency, elevated levels of total homocysteine and methylmalonic acid indicate cobalamin deficiency, and elevated levels of total homocysteine combined with normal levels of methylmalonic acid indicate folic acid deficiency.

19. A method for detecting a deficiency of cobalamin, folate, or both in warm-blooded animals and distinguishing therebetween by assaying body fluids for the presence of elevated levels of total homocysteine and methylmalonic acid, wherein the total homocysteine assay is performed according to the method of claim 7, and wherein normal levels of total homocysteine indicate no cobalamin or folic acid deficiency, elevated levels of total homocysteine and methylmalonic acid indicate cobalamin deficiency, and elevated levels of total homocysteine combined with normal levels of methylmalonic acid indicate folic acid deficiency.

20. The method of claim 18 wherein said assay for the presence of elevated levels of total homocysteine comprises subjecting a sample of body fluid to chromatography.

21. The method of claim 20 wherein said assay for the presence of elevated levels of total homocysteine comprises subjecting a sample of body fluid to high performance liquid chromatography with an electrochemical detector set to respond to thiol groups, and comparing the results with a standard curve to determine the amount of total homocysteine present in the original sample.

22. The method of claim 18 wherein the assay for the presence of elevated levels of total homocysteine comprises converting any homocysteine present in the sample to labelled S-adenosylhomocysteine by exposure to radioactively labelled adenosine and S-adenosylhomocysteine hydrolase, and quantifying said labelled S-adenosylhomocysteine by appropriate detection means.

23. The method of claim 18 wherein the methylmalonic acid is assayed by the process of:
  (a) combining a tissue sample with an internal reference standard comprising a known amount of methylmalonic acid labelled with a stable isotope marker;
  (b) measuring the relative amounts of labelled and unlabelled methylmalonic acid present with a mass spectrophotometer;
  (c) calculating the ratio of labelled to unlabelled methylmalonic acid present; and
  (d) deriving the amount of unlabelled methylmalonic acid present in said given sample.

24. The method of claim 23 wherein said labelled and unlabelled methylmalonic acid is derivatized after step (a) and before step (b).

25. The method of claim 24, wherein said derivatized amino acids are silyl derivatives.

26. The method of claim 25, wherein said silyl derivatives are obtained by exposing said methylmalonic acid to N-methyl-N-(t-butyldimethylsilyl)trifluoroacetamide.

27. The method of claim 23 or 24 wherein said internal reference standard in step (a) comprises a known amount of deuterated methylmalonic acid.

28. The method of claim 26, comprising the additional step of partially purifying the methylmalonic acid after step (a) and before step (b).

29. A method of treating a human for cobalamin deficiency which comprises assaying at least one body tissue or fluid from said human for the presence of cobalamin deficiency according tot he method of claim 13, and administering to said human an amount of cobalamin sufficient to return the total homocysteine levels to normal.

30. A method of treating a human for cobalamin deficiency which comprises assaying at least one body tissue or fluid from said human for the presence of cobalamin deficiency according to the method of claim 18, and administering to said human an amount of cobalamin sufficient to return the total homocysteine levels to normal.

31. A method of treating a human for folic acid deficiency which comprises assaying at least one body tissue or fluid from said human for the presence of folic acid deficiency according to the method of claim 13, and administering to said human an amount of folic acid sufficient to return the total homocysteine levels to normal.

32. A method of treating a human for folic acid deficiency which comprises assaying at least one body tissue or fluid from said human for the presence of folic acid deficiency according to the method of claim 18, and administering to said human an amount of folic acid sufficient to return the total homocysteine levels to normal.

33. The method for detecting a deficiency of cobalamin or folate, as recited in claim 13, wherein said assaying comprises the step of determining total homocysteine in a human body fluid.

34. The method for detecting a deficiency of cobalamin, folate, or both, as recited in claim 18, wherein said assaying comprises the step of determining elevated levels of total homocysteine and methylmalonic acid in human body fluid.

* * * * *

(12) EX PARTE REEXAMINATION CERTIFICATE (8895th)
United States Patent
Allen et al.

(10) Number: US 4,940,658 C1
(45) Certificate Issued: Mar. 13, 2012

(54) ASSAY FOR SULFHYDRYL AMINO ACIDS AND METHODS FOR DETECTING AND DISTINGUISHING COBALAMIN AND FOLIC ACID DEFICIENCY

(75) Inventors: Robert H. Allen, Englewood, CO (US); Sally P. Stabler, Denver, CO (US); John Lindenbaum, New York, NY (US)

(73) Assignee: The Trustees of Columbia University, New York, NY (US)

Reexamination Request:
No. 90/008,305, Oct. 23, 2006

Reexamination Certificate for:
Patent No.: 4,940,658
Issued: Jul. 10, 1990
Appl. No.: 06/933,553
Filed: Nov. 20, 1986

(51) Int. Cl.
*G01N 33/82* (2006.01)
*G01N 33/68* (2006.01)

(52) U.S. Cl. .............. 435/4; 435/18; 436/120; 436/173; 436/174; 436/8; 436/825; 436/86; 514/249; 514/52

(58) Field of Classification Search .............. None
See application file for complete search history.

(56) References Cited

To view the complete listing of prior art documents cited during the proceeding for Reexamination Control Number 90/008,305, please refer to the USPTO's public Patent Application Information Retrieval (PAIR) system under the Display References tab.

*Primary Examiner*—Padmashri Ponnaluri

(57) ABSTRACT

Method for determining levels of sulfhydryl amino acids, particularly total homocysteine levels in samples of body tissue from warm-blooded animals, methods of detecting cobalamin and folic acid deficiency using an assay for total homocysteine levels, and methods for distinguishing cobalamin from folic acid deficiency using an assay for total homocysteine levels in conjunction with an assay for methylmalonic acid.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 13, 15-17 and 33 is confirmed.

Claims 1-12, 14, 18-32 and 34 were not reexamined.

\* \* \* \* \*